United States Patent [19]

Fortin et al.

[11] Patent Number: 5,360,815

[45] Date of Patent: Nov. 1, 1994

[54] HETEROARYL CINNAMIC ACIDS AS INHIBITORS OF LEUKOTRIENE BIOSYNTHESIS

[75] Inventors: Rejean Fortin, Montreal; Yves Girard, Ile Bizard; Erich Grimm, Baie d'Urfe, all of Canada; John Hutchinson, Philadelphia, Pa.; John Scheigetz, Dollard des Ormeaux, Canada

[73] Assignee: Merck Frosst Canada, Inc., Kirkland, Canada

[21] Appl. No.: 81,506

[22] Filed: Jun. 23, 1993

[51] Int. Cl.$^5$ .................. A61K 31/38; A61K 31/335; A61K 31/385; A61K 31/35

[52] U.S. Cl. .................... 514/432; 514/433; 514/436; 514/438; 514/444; 514/452; 514/460; 514/461; 514/568; 549/14; 549/21; 549/28; 549/60; 549/78; 549/364; 549/365; 549/370; 549/372; 549/397; 549/414; 549/416; 549/423; 549/468; 549/502; 562/468

[58] Field of Search ............... 549/416, 397, 423, 28, 549/414, 78, 60, 502, 14, 21, 370, 372, 365, 364; 562/468; 514/336, 345, 277, 432, 444, 438, 460, 461, 568, 433, 436, 452

[56] References Cited

U.S. PATENT DOCUMENTS 5,225,438 7/1993 Dowell et al. ............... 549/423
5,252,599 10/1993 Girard et al. ............... 549/414

FOREIGN PATENT DOCUMENTS

0462813A2 12/1991 European Pat. Off. .
0462830A2 12/1991 European Pat. Off. .
0462831A2 12/1991 European Pat. Off. .

Primary Examiner—Richard L. Raymond
Assistant Examiner—Mary C. Cebulak
Attorney, Agent, or Firm—Mollie M. Yang; David L. Rose

[57] ABSTRACT

Compounds having the formula I:

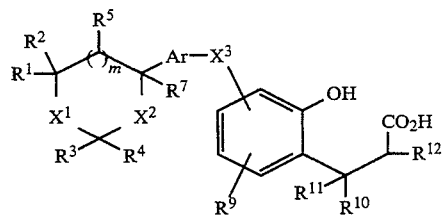

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

10 Claims, No Drawings

HETEROARYL CINNAMIC ACIDS AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene B4 (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is convened to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

European Patent Application 488,602 (ICI) discloses compounds of structure 1 as inhibitors of 5-lipoxygenase. These compounds differ from the present invention most notably in the nature of $X^1$ of the reference structure which is defined as $-X_4-CR_2-$ or $-CR_2-X_4-$ whereas the present compounds have a carbon atom ($CR^{10}R^{11}$) to which is attached a carboxyl-carrying chain. EP 129,906 (Hoffmann-LaRoche) describes compounds such as 2 as intermediates with no disclosed biological activity and lacking the $X^1/X^2$-containing ring of the present compounds. Compounds of structure 3 are disclosed as lipoxygenase inhibitors in EP 196,184 and WO 90/01929 (Wellcome), differing from the present compounds in the nature of their X link and the substitution on their Ar unit. Compounds related to 4 are disclosed by Schrötter et al. as having anti-infective/anti-septic properties. There are structural differences from the present compounds, such as the absence of a carboxylic acid and the absence of the $X^1/X^2$-containing ring.

1. 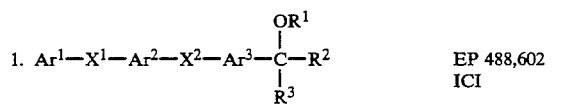 EP 488,602 ICI

2. 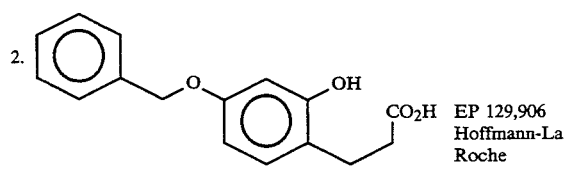 EP 129,906 Hoffmann-La Roche

3. 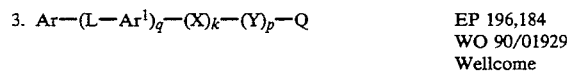 EP 196,184 WO 90/01929 Wellcome

4. 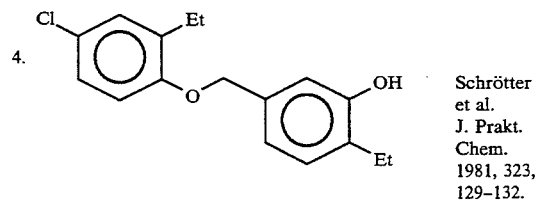 Schrötter et al. J. Prakt. Chem. 1981, 323, 129-132.

SUMMARY OF THE INVENTION

The present invention relates to heteroaryl cinnamic acids having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The compounds of the present invention may be represented by formula I:

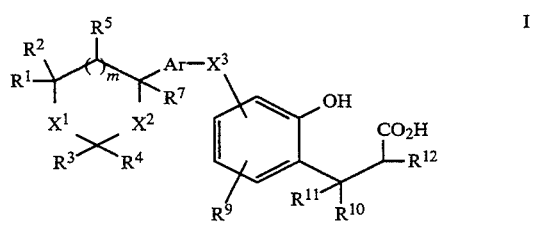

wherein:

$R^1$ is H, OH, lower alkyl, or lower alkoxy;

$R^2$ is H, lower alkyl or together with $R^1$ forms a double bonded oxygen (=O);

$R^3$ is H, lower alkyl, hydroxy lower alkyl, or lower alkoxy lower alkyl; or $R^1$ is joined to $R^3$ to form a carbon bridge of 2 or 3 carbon atoms, or a mono-oxa carbon bridge of 1 or 2 carbon atoms, said bridge optionally containing a double bond;

$R^4$ is H or lower alkyl;

$R^5$ is H, OH, lower alkyl, or lower alkoxy;

$R^6$ is H or lower alkyl, or two $R^6$ groups attached to the same carbon may form a saturated ring of 3 to 8 members;

$R^7$ is H, OH, lower alkyl, lower alkoxy, cycloalkyl lower alkoxy, lower alkylthio, or lower alkylcarbonyloxy;

$R^8$, $R^9$, and $R^{13}$ is each independently H, halogen, lower alkyl, hydroxy, lower alkoxy, lower alkylthio, $CF_3$, CN, or $COR^{14}$;

$R^{10}$ is H, lower alkyl, or aryl-$(R^{13})_2$, wherein aryl is a 5-membered aromatic ring wherein one carbon atom is replaced by O or S and 0-3 carbon atoms are replaced by N; a 5-membered aromatic ting wherein 1-4 carbon atoms are replaced by N; a 6-membered aromatic ting wherein 0-3 carbon atoms are replaced by N; 2- or 4-pyranone; 2- or 4-pyridinone; or a bicyclic 8-, 9-, or 10-membered aromatic ring wherein 0-2 carbon atoms are replaced by either O or S or a combination thereof and 0-3 carbon atoms are replaced by N;

$R^{11}$ and $R^{12}$ is each independently H or lower alkyl, or $R^{11}$ and $R^{12}$ together form a bond;

$R^{14}$ is H or lower alkyl;

$X^1$ is O, S, S(O), $S(O)_2$, or $CH_2$;

$X^2$ is O, S, or $CHR^6$;

$X^3$ is O, S, S(O), S(O)$_2$, OC(R$^6$)$_2$, C(R$^6$)$_2$O, SC(R$^6$)$_2$, C(R$^6$)$_2$S, or [C(R$^6$)$_2$]$_n$;

Ar is arylene-(R$^8$)$_2$, wherein arylene is a 5-membered aromatic ring containing one O or S and with 0–2 carbon atoms replaced by N; a 5-membered aromatic ring wherein 1–3 carbon atoms are replaced by N; a 6-membered aromatic ring wherein 0–3 carbon atoms are replaced by N; 2- or 4-pyranone; or 2- or 4-pyridinone;

m is 0 or 1;
n is 1 or 2;
or a pharmaceutically acceptable salt thereof.

A preferred embodiment of the present invention is represented by Formula Ia:

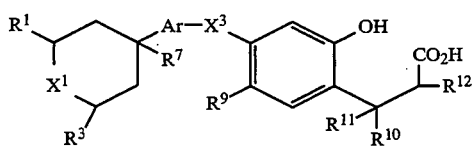

wherein:
R$^1$ and R$^3$ is each independently H or CH$_3$, or together are —CH$_2$CH$_2$—, —CH$_2$O—, or —OCH$_2$—;
R$^7$ is OH, OMe, OEt, or OCH$_2$c-Pr;
R$^9$ is H or Cl;
R$^{10}$ is H, Me, Pr, Ph, 3-Fu, or 3-Th;
R$^{11}$ and R$^{12}$ is each H, or R$^{11}$ and R$^{12}$ together are a bond;
X$^3$ is —CH$_2$O— or —OCH$_2$—; and
Ar is 3-Phe, 5,3-Pye, 4,2-Pye, 2,4-Pye, 6,2-Pye, or 2,4-Tze;

A more preferred embodiment of the present invention is represented by Formula Ib:

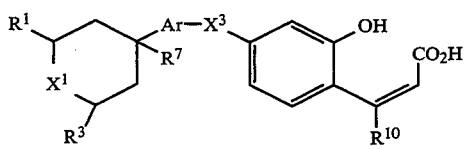

wherein:
R$^1$ and R$^3$ is each H or together are —CH$_2$O or —OCH$_2$—;
R$^7$ is OH or OMe;
R$^{10}$ is Ph, 3-Fu, or 3-Th;
X$^3$ is —CH$_2$O— or —OCH$_2$—;
Ar is 3-Phe or 6,2-Pye.

Definitions

The following abbreviations have the indicated meanings:
Ac = acetyl
AIBN = 2,2'-azobisisobutyronitrile
Bn = benzyl
DHP = 3,4-dihydro-2H-pyran
DIPHOS = 1,2-bis(diphenylphosphino)ethane
DMAP = 4-(dimethylamino)pyridine
DMF = N,N-dimethylformamide
DMSO = dimethyl sulfoxide
Et$_3$N = triethylamine
Fu = furyl
Fur = furandiyl
KHMDS = potassium hexamethyldisilazane
LDA = lithium diisopropylamide
Ms = methanesulfonyl = mesyl
MsO = methanesulfonate = mesylate
NBS = N-bromosuccinimide
NCS = N-chlorosuccinimide
NSAID = non-steroidal anti-inflammatory drug
PCC = pyridinium chlorochromate
PDC = pyridinium dichromate
Ph = phenyl
Phe = benzenediyl
Pye = pyridinediyl
r.t. = room temperature
rac. = racemic
Tf = trifluoromethanesulfonyl = trifiyl
TfO = trifluoromethanesulfonate = triflate
Th = 2- or 3-thienyl
THF = tetrahydrofuran
Thi = thiophenediyl
Ts = p-toluenesulfonyl = tosyl
TsO = p-toluenesulfonate = tosylate
Tz = 1H (or 2H)-tetrazol-5-yl
Tze = thiazoldiyl
C$_3$H$_5$ = allyl
BuLi = Butyl Lithium Alkyl Group Abbreviations Me = methyl
Et = ethyl
n-Pr = normal propyl
i-Pr = isopropyl
n-Bu = normal butyl
i-Bu = isobutyl
s-Bu = secondary butyl
t-Bu = tertiary butyl
c-Pr = cyclopropyl
c-Bu = cyclobutyl
c-Pen = cyclopentyl
c-Hex = cyclohexyl Alkyl, alkenyl, and alkynyl mean linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Cycloalkyl" refers to a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, aldamantyl, cyclododecylmethyl, 2-ethyl-1-bicyclo[4.4.0]decyl, and the like.

"Alkenyl" includes "lower alkenyl" and means alkenyl groups of 2 to 20 carbon atoms. Examples of alkenyl groups are allyl, 5-decen-1-yl, 2-dodecen-1-yl, and the like.

"Lower alkenyl" means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

"Cycloalkenyl" means alkenyl groups of 3 to 20 carbon atoms, which include a ring of 3 to 12 carbon atoms, and in which the alkenyl double bond maybe located anywhere in the structure. Examples of cycloalkenyl groups are cyclopropen-1-yl, cyclohexen- 3-yl, 2-vinyladamant-1-yl, 5-methylenedodec-1-yl, and the like.

"Alkynyl" includes "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" means alkynyl groups of 2 to 7 carbon atoms. Examples of lower alkynyl groups include ethynyl, propargyl, 3-methyl-1-pentynyl, 2-heptynyl, and the like.

"Cycloalkynyl" means groups of 5 to 20 carbon atoms, which include a ring of 3 to 20 carbon atoms. The alkynyl triple bond may be located anywhere in the group, with the proviso that if it is within a ring, such a ring must be of 10 members or greater. Examples of "cycloalkynyl" are cyclododecyn-3-yl, 3-cyclohexyl-1-propyn-1-yl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched, or cyclic configuration. Examples of lower alkylthio groups include methylthio, propylthio, isopropylthio, cycloheptylthio, etc. By way of illustration, the propylthio group signifies —$SCH_2CH_2CH_3$.

"Lower alkylsulfonyl" means alkylsulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, etc. By way of illustration, the 2-butylsulfonyl group signifies —$S(O)_2CH(CH_3)CH_2CH_3$.

"Alkycarbonyl" includes "lower alkylcarbonyl" and means alkylcarbonyl groups of 1 to 20 carbon atoms of a straight, branched, or cyclic configuration. Examples of alkylcarbonyl groups are 2-methylbutanoyl, octadecanoyl, 11-cyclohexylundecanoyl, and the like. Thus, the 11-cyclohexylundecanoyl group is c—Hex—$(CH_2)_{10}$—CO—.

"Lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, cyclohexylacetyl, etc. By way of illustration, the 2-methylbutanoyl group signifies —$COCH(CH_3)CH_2CH_3$.

Halogen includes F, Cl, Br, and I.

It is intended that the definitions of any substituent (e.g., $R^6$, $R^8$, etc.) in a particular molecule be independent of its definitions elsewhere in the molecule. Thus, $C(R^6)_2$ represents —$CH_2$—, —CHEt—, —$C(Et)_2$—, etc.

Examples of Ar are furan, thiophene, oxazole, thiazole, 1,3,4-oxadiazole, 1,3,4-thiadiazole, 1,2,5-oxadiazole, 1,2,5-thiadiazole, pyrrole, imidazole, 1,3,4-triazole, benzene, pyridine, pyrazine, pyrimidine, pyridazine, 1,2,3-triazine, 1,2,4-triazine, and 1,3,5-triazine.

Examples of aryl in $R^{10}$ are furan, thiophene, oxazole, thiazole, isoxazole, isothiazole, 1,3,4-oxadiazole, 1,3,4-thiadiazole, 1,2,5-oxadiazole, 1,2,5-thiadiazole, pyrrole, pyrazole, imidazole, 1,3,4-triazole, tetrazole, benzene, pyridine, pyrazine, pyrimidine, pyridazine, 1,2,3-triazine, 1,2,4-triazine, 1,3,5-triazine, thieno[2,3-b]furan, thieno[3,2-b]pyrrole, indole, benzofuran, benzothiophene, benzimidazole, benzoxazole, benzothiazole, benzo[2,1,3]thiadiazole, furano[3,2-b]pyridine, naphthalene, quinoline, isoquinoline, quinoxaline, quinazoline, cinnoline, phthalazine, 1,8-naphthyridine, and the like.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carder and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts. The compounds of the present invention are most conveniently isolated and used as their disodium salts. The free phenolic acids can be isolated by careful acidification of a solution or suspension of the salts in an ice-cooled bath.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, and 17) proliferation of myoblastic leukemia cells.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are: (A) an ethanol-induced lesion assay and (B) an indomethacin-induced ulcer assay and are described in EP 140,684.

Dose Rangers

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carders such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of | 1 mL |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) propionic acid derivatives;
(2) acetic acid derivatives;
(3) fenamic acid derivatives;
(4) oxicams; and
(5) biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or—CH₂CH₂COOH group (which optionally can be in the form of a pharmaceutically acceptable salt group, e.g., —CH(CH₃)COO—Na⁺ or —CH₂CH₂COO—Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO—Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

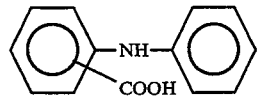

which can bear a variety of substituents and in which the free —COOH group can be in the form of a pharmaceutically acceptable salt group, e.g., —COO—Na⁺.

The biphenylcarboxylic acid derivatives which can be used comprise: diflunisal and flufenisal. Structurally related biphenylcarboxylic acid derivatives have similar analgesic anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

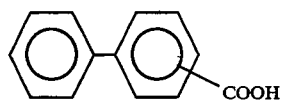

which can bear a variety of substituents and in which the free —COOH group can be in the form of a pharmaceutically acceptable salt group, e.g., —COO—Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

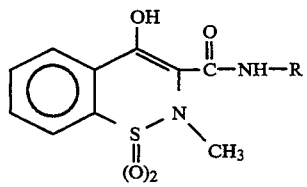

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, oxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions comprising the Formula I compounds may also contain inhibitors of the biosynthesis of the leukotrienes such as are disclosed in EP 138,481 (Apr.24, 1985), EP 115,394 (August 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr, 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981 ), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981 ), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods. The substituents are the same as in Formula I except where defined otherwise.

Scheme I

Compounds of formula 1A can be synthesized using the routes given in Scheme 1. The resorcinol derivative II can be acylated by heating a mixture of II, an aliphatic acid (or aromatic acid) in a solvent such as 1,2-dichloroethane in the presence of a Lewis acid such as $ZnCl_2$ to yield the acyl derivative III. Reaction of III with a stabilized Wittig reagent such as methyl (triphenylphosphoranylidene)acetate in an organic solvent, for example toluene, at reflux allows for the preparation of the coumarin IV. An alternative preparation of coumarin IV requires heating the resorcinol derivative II with a substituted β-keto ester in the presence of, for example, polyphosphoric acid.

Selective alkylation of the intermediate III, can be achieved by stirring a mixture of III, an electrophile of general structure V (where X=Cl, Br, I, OMs, or OTs) in a dipolar aprotic solvent such as DMF with an inorganic base like $Cs_2CO_3$. Such an alkylation of III affords the intermediate VI. In a similar fashion, the phenol of coumarin IV can be converted into the coumarin derivative VII. An alternative procedure to prepare VII involves the coupling of IV with a benzylic alcohol of general structure V (where X=OH) in the presence of an azidodicarboxylate derivative (e.g., diethyl azidodicarboxylate) and a phosphine such as triphenylphosphine in an organic solvent such as THF. Following the procedure described above for the conversion of III to IV, the intermediate VI can also be converted to coumarin derivatives VII.

Scheme II

Coumarin derivatives of formula IB, in which them is a carbon substituent at C-7 of the coumarin, can be prepared as shown in Scheme II. The 7-hydroxycoumarin compound IV (from Scheme I) can be transformed to the corresponding triflate analogue VIII by reaction with trifluoromethanesulfonic anhydride in the presence of an organic base (for example, $Et_3N$) in a chlorinated solvent such as dichloromethane. Reaction of VIII with a palladium(0) species such as tetrakis (triphenylphosphin)palladium(0), an organic base (e.g., $Et_3N$) and methanol in a dipolar aprotic solvent (for example, DMSO) under an atmosphere of carbon monoxide results in the formation of IX. The ester IX can be saponified by heating a solution of IX in an alcoholic organic solvent such as methanol and THF with an inorganic base such as aqueous LiOH. Acidification of the reaction mixture using, for example, aqueous HCl and addition of an organic solvent such as diethyl ether then affords the acid X. This acid can be chemoselectively reduced by adding a chloroformate (such as isobutylchloroformate) to a solution of X and an organic base (e.g., $Et_3N$) in a solvent such as THF. A reducing agent, for example $NaBH_4$, is then added and the alcohol XI is thus obtained. Conversion of XI to the coumarin derivative XIII can be achieved using the procedure described in Scheme I for the coupling of IV with the alcohol V (where X=OH).

Scheme III

Sulfur-linked compounds of general structure IC may be obtained via the route described in Scheme III. The phenol IV (from Scheme I) may be treated with an inorganic base such as NaH in an appropriate organic solvent (such as THF) followed by the addition of dimethylthiocarbamyl chloride; this results in the formation of XIV. Thermolysis of XIV then yields XV. Upon treatment of XV with an inorganic base (for example NaOMe in MeOH) at reflux followed by acidification of the reaction mixture, the thiol XVI is formed. The thiol XVI can then be coupled with an aromatic bromide or iodide of general formula XVII in the presence of copper (I) salts such as CuCl or CuBr to yield coumarin derivatives XVIII.

Scheme IV

Coumarins of formula I (wherein $R^{11}$ and $R^{12}$ form a bond) can be hydrogenated, according to Scheme IV, to give the corresponding derivatives m which $R^{11}$ and $R^{12}$ are both hydrogen. Stirring a solution of VII, XIII or XVIII in an organic solvent such as THF and methanol, with a catalyst (for example Pd on carbon) under an atmosphere of hydrogen gas gives rise to the saturated product XIX (wherein $R^{11}=R^{12}=H$).

The hydrolysis of coumarins VII (Scheme I), XIII (Scheme II), XVIII (Scheme III), and XIX (Scheme IV) using an inorganic base such as NaOH in a solvent such as EtOH/H$_2$O provides compounds of Formula I of the present invention. It will be evident to one skilled in the art that a variety of cationic salt forms of I can be prepared in this way or by cation exchange processes.

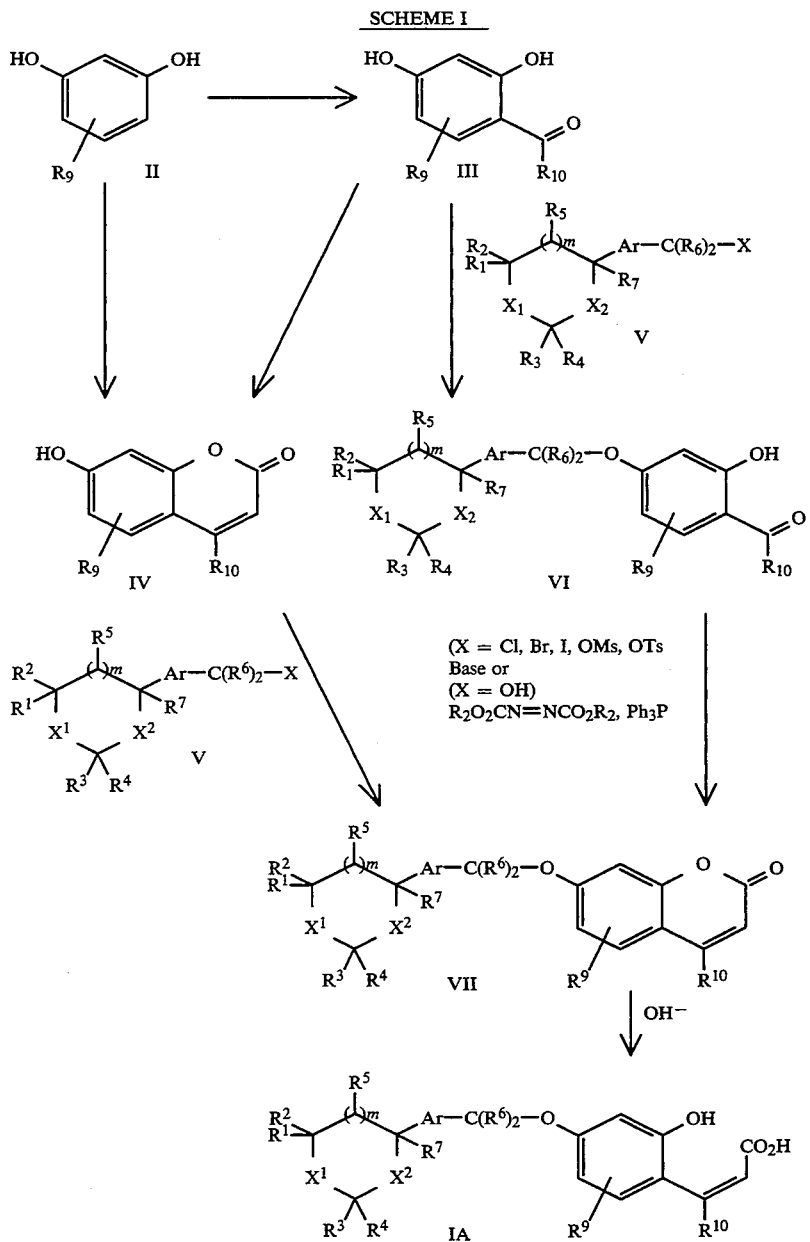

-continued
SCHEME II
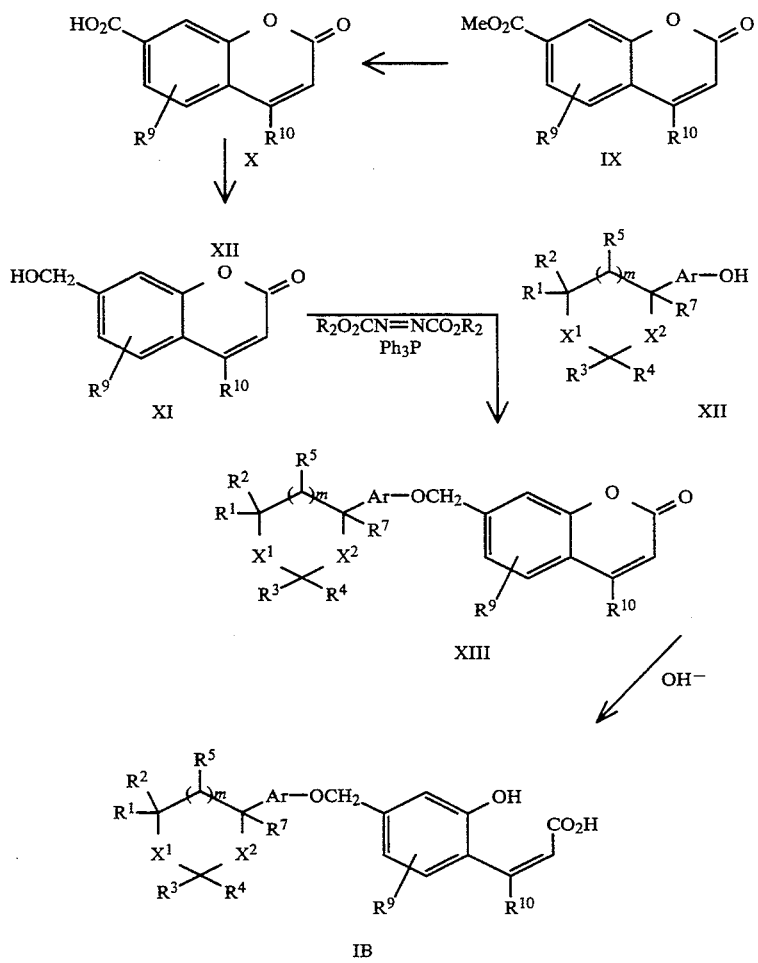
SCHEME III
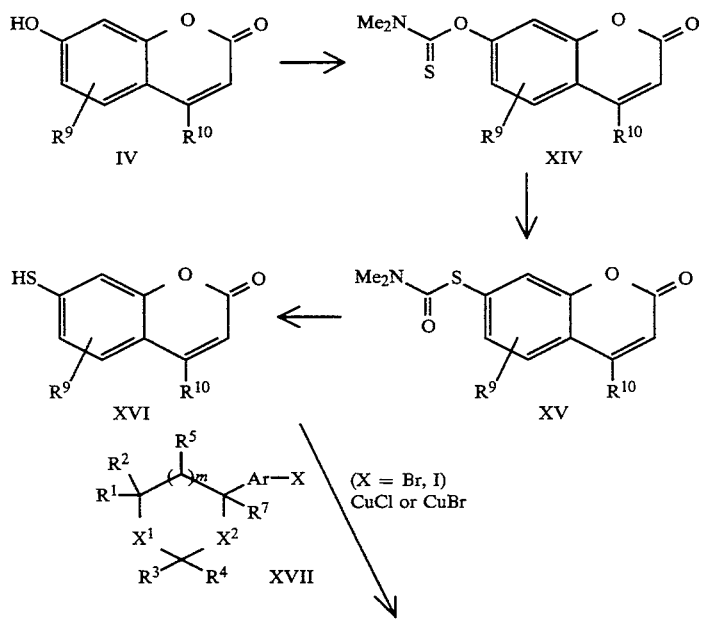

SCHEME III

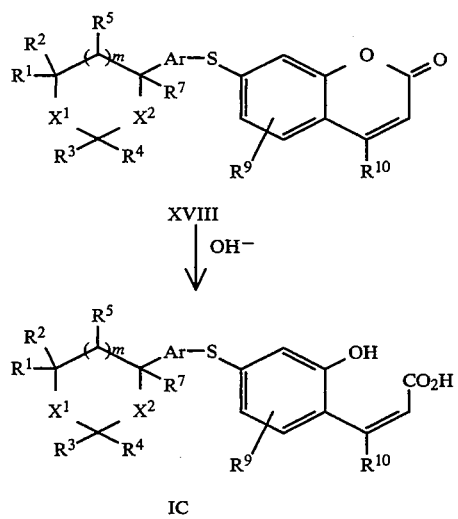

SCHEME IV

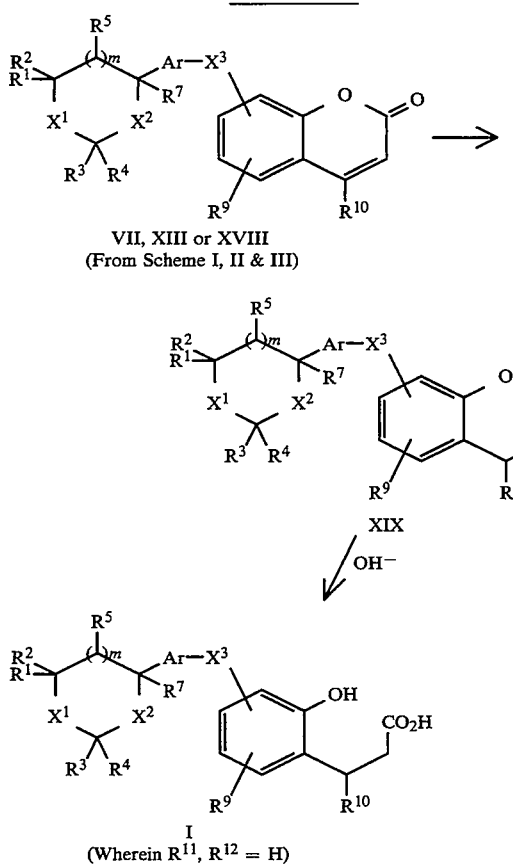

Representative Compounds

Tables 1 and 2 illustrate compounds of formulae Ic and Id, which are representative of the present invention.

TABLE 1

Ic

| EX. | $R^1$ | $R^3$ | $R^7$ | $R^9$ | $R^{10}$ | Ar |
|---|---|---|---|---|---|---|
| 1 | H | H | OMe | H | H | 3-Phe |
| 2 | H | H | OMe | H | Me | 3-Phe |
| 3 | H | H | OMe | Cl | Me | 3-Phe |
| 4 | H | H | OMe | H | n-Pr | 3-Phe |
| 5 | H | H | OH | H | Ph | 3-Phe |
| 6 | H | H | OMe | H | Ph | 3-Phe |
| 7 | H | H | OH | H | 3-Fu | 3-Phe |
| 8 | H | H | OMe | H | 3-Fu | 3-Phe |
| 9 | H | H | OH | H | 3-Th | 3-Phe |
| 10 | H | H | OMe | H | 3-Th | 3-Phe |
| 11 | H | H | OEt | H | 3-Th | 3-Phe |
| 12 | H | H | OCH2c-Pr | H | 3-Th | 3-Phe |
| 13 | H | H | OH | H | 3-Th | 5,3-Pye |
| 14 | H | H | OMe | H | 3-Th | 5,3-Pye |
| 15 | —CH2O— | | OH | H | 3-Th | 3-Phe |
| 16 | —CH2O— | | OMe | H | 3-Th | 3-Phe |
| 17 | —CH2O— | | OH | H | 3-Fu | 3-Phe |
| 18 | —CH2O— | | OMe | H | 3-Fu | 3-Phe |
| 19 | —CH2O— | | OH | H | Ph | 3-Phe |
| 20 | —CH2O— | | OMe | H | Ph | 3-Phe |
| 21 | —CH2CH2— | | OH | H | 3-Th | 3-Phe |
| 22 | —CH2CH2— | | OMe | H | 3-Th | 3-Phe |
| 23 | H | H | OH | H | 3-Th | 6,2-Pye |
| 24 | H | H | OMe | H | 3-Th | 6,2-Pye |
| 25 | —CH2O— | | OH | H | 3-Th | 6,2-Pye |
| 26 | —CH2O— | | OMe | H | 3-Th | 6,2-Pye |

TABLE 2

Id

| EX. | $R^1$ | $R^3$ | $R^7$ | $R^{10}$ | Ar |
|---|---|---|---|---|---|
| 27 | H | H | OH | Ph | 5-(3-FPhe) |
| 28 | H | H | OMe | Ph | 5-(3-FPhe) |
| 29 | H | H | OH | 3-Th | 5-(3-FPhe) |
| 30 | H | H | OMe | 3-Th | 5-(3-FPhe) |
| 31 | H | H | OH | 3-Fu | 5-(3-FPhe) |

TABLE 2-continued $$\text{R}^1\text{-CH(O)-CH}_2\text{-C(R}^3\text{)(Ar)(R}^7\text{)-O-CH}_2\text{-C}_6\text{H}_3(\text{OH})\text{-CR}^{10}\text{=CH-CO}_2\text{H} \quad \text{Id}$$

| EX. | $R^1$ | $R^3$ | $R^7$ | $R^{10}$ | Ar |
|---|---|---|---|---|---|
| 32 | H | H | OMe | 3-Fu | 5-(3-FPhe) |
| 33 | —CH$_2$O— |  | OH | Ph | 5-(3-FPhe) |
| 34 | —CH$_2$O— |  | OMe | Ph | 5-(3-FPhe) |
| 35 | —CH$_2$O— |  | OH | 3-Th | 5-(3-FPhe) |
| 36 | —CH$_2$O— |  | OMe | 3-Th | 5-(3-FPhe) |
| 37 | —CH$_2$O— |  | OH | 3-Fu | 5-(3-FPhe) |
| 38 | —CH$_2$O— |  | OMe | 3-Fu | 5-(3-FPhe) |
| 39 | —CH$_2$CH$_2$— |  | OH | 3-Th | 5-(3-FPhe) |
| 40 | —CH$_2$CH$_2$— |  | OMe | 3-Th | 5-(3-FPhe) |
| 41 | H | H | OH | 3-Th | 5,3-Pye |
| 42 | H | H | OMe | 3-Th | 5,3-Pye |
| 43 | H | H | OH | 3-Th | 6,2-Pye |
| 44 | H | H | OMe | 3-Th | 6,2-Pye |
| 45 | —CH$_2$O— |  | OH | 3-Th | 6,2-Pye |
| 46 | —CH$_2$O— |  | OMe | 3-Th | 6,2-Pye |
| 47 | —CH$_2$CH$_2$— |  | OH | 3-Th | 6,2-Pye |
| 48 | —CH$_2$CH$_2$— |  | OMe | 3-Th | 6,2-Pye |
| 49 | —CH$_2$O— |  | OH | 3-Th | 3-Phe |
| 50 | —CH$_2$O— |  | OMe | 3-Th | 3-Phe |
| 53 | H | H | OMe | 3-Th | 5-(3-BrPhe) |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000x g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000x g fraction from S19 cells infected with the recombinant baculovirus rvH5LO(8-1) containing the coding region sequence for human 5-lipoxygenase is prepared as described by Denis et al. (J. Biol. Chem., 266, 5072–5079 (1991)). The enzymatic activity is measured, using a spectro-photometric assay from the optimal rate of conjugated diene formation ($A_{234}$) using the procedure described by Riendeau et al. (Biochem. Pharmacol. 38, 2323-2321, (1989)) with minor modifications. The incubation mixture contains 50 mM sodium phosphate pH 7.4, 0.2 mM ATP, 0.2 mM CaCl$_2$, 20 $\mu$M arachidonic acid (5 $\mu$L from a 100-fold concentrated solution in ethanol), 12 $\mu$g/mL phosphatidylcholine, an aliquot of the 100,000x g fraction (2–10 $\mu$L) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software (Hewlett Packard). Enzymatic activity is calculated from the optimal rate of the reaction by a linear fit of the variation of $A_{234}$ during the first twenty seconds using the least square method for the equation $A_{234} = V_o t + A_o$ where $V_o$ is the rate, t is the time, and $A_o$ is the absorbance at zero time. The results are expressed as percentages of inhibition of the reaction rate relative to controls (typically between 0.15–0.21 AU/min) containing the DMSO vehicle.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15–24 hr. the rats are sacrificed (CO$_2$) and the cells from the peritoneal cavity are recovered by lavage with 20 mL of buffer (Eagles MEM containing 30 mM HEPES adjusted to pH 7.4 with NaOH). The cells are pelleted (350x g, 5 min.), resuspended in buffer with vigorous shaking, filtered through lens paper, recentrifuged and finally suspended in buffer at a concentration of 10 cells/mL. A 500 $\mu$L aliquot of PMN suspension and test compound are preincubated for 2 minutes at 37° C., followed by the addition of 10 $\mu$M calcium ionophore A-23187. The suspension is stirred for an additional 4 minutes then bioassayed for LTB$_4$ content by adding an aliquot to a second 500 $\mu$L portion of the PMN at 37° C. The LTB$_4$ produced in the first incubation causes aggregation of the second PMN, which is measured as a change in light transmission. The size of the assay aliquot is chosen to give a submaximal transmission change (usually $-70\%$) for the untreated control. The percentage inhibition of LTB$_4$ formation is calculated from the ratio of transmission change in the sample to the transmission change in the compound-free control.

Human Polymorphonuclear (PMN) Leukocyte LTB$_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum (Scand. J. Clin. Lab, Invest., 21 (Supp 97), 77 (1968)). Contaminating erythrocytes are removed by lysis following exposure to ammonium chloride (0.16M) in Tris buffer (pH 7.65), and the PMNs are resuspended at 5x 105 cells/mL in HEPES (15 mM)-buffered Hanks balanced salt solution containing Ca$^{2+}$(1.4 mM) and Mg$^{2+}$(0.7 mM), pH 7.4.

B. Generation and Radioimmunoassay of LTB$_4$. PMNs (0.5 mL; 2.5x 105 cells) are placed in plastic tubes and incubated (37° C., 2 min) with test compounds at the desired concentration or vehicle (DMSO, final concentration 0.2%) as control. The synthesis of LTB$_4$ is initiated by the addition of calcium ionophore A23187 (final concentration 10 $\mu$M) or vehicle in control samples and allowed to proceed for 5 minutes at 37° C. The reactions are then terminated by the addition of cold methanol (0.25 mL) and samples of the entire PMN reaction mixture are removed for radioimmunoassay of LTB$_4$.

Samples (50 μL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-LTB$_4$ (10 nCi in 100 μL RIA buffer) and LTB$_4$-antiserum (100 μL of a 1:3000 dilution in RIA buffer) are added and the tubes vortexed. Reactants are allowed to equilibrate by incubation overnight at 4° C. To separate antibody-bound from free LTB$_4$, aliquots (50 μL) of activated charcoal (3% activated charcoal in RIA buffer containing 0.25% Dextran T-70) are added, the tubes vortexed, and allowed to stand at room temperature for 10 minutes prior to centrifugation (1500x g; 10 min; 4° C.). The supernatant containing antibody-bound LTB$_4$ are decanted into vials and Aquasol 2 (4 mL) is added. Radioactivity is quantified by liquid scintillation spectrometry. The specificity of the antiserum and the sensitivity of the procedure have been described by Rokach et al., *Prostaglandins Leukotrienes and Medicine*, 13, 21 (1984). The amount of LTB$_4$ produced in test and control samples is calculated. Inhibitory dose-response curves are constructed using a four-parameter algorithm and from these the IC$_{50}$ values are determined.

Human Whole Blood Assay in Vitro for LTB$_4$ Production

Fresh blood is collected in heparinized tubes by venipuncture from human volunteers. A 500 μL aliquot is incubated with one of the test compounds at final concentrations varying from. 3 nM to 3 mM at 37° C. for 15 min. Drug stock solutions are made up in DMSO and 1 μL of the stock solution is added to each assay tube. The blood is then incubated with A23187 (in 5 μL autologous plasma, 25 μM final concentration) at 37° C. for 30 min. At the end of incubation, plasma is obtained (12,000x g, 15 min) and a 100 μL aliquot is added to 400 μL methanol for protein precipitation. The mixture is vortexed, centrifuged and the supernatant stored at −70° C. until assayed for LTB$_4$ by standard RIA.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyser, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post sensitization. In order to eliminate the serotonin component of the response, rats are pretreated intravenously 5 minutes prior to aerosol challenge with 3.0 μg/kg of methysergide. Rats are then exposed to an aerosol of 3 % EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an ED$_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene D$_4$ (LTD$_4$) or Ascaris suum antigen, 1:25 dilution.

Following challenge, each minute of data is calculated by computer as a percent change from control values for each respiratory parameter including airway resistance (R$_L$) and dynamic compliance (C$_{dyn}$). The results for each test compound are subsequently obtained for a minimum period of 60 minutes post challenge which are then compared to previously obtained historical baseline control values for as that monkey. In addition, the overall values for 60 minutes post-challenge for each monkey (historical baseline values and test values) are averaged separately and are used to calculate the overall percent inhibition of LTD$_4$ or Ascaris antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

A. Rationale. Certain allergic sheep with known sensitivity to a specific antigen (Ascaris suum) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods. Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, NC) and b) they have previously responded to inhalation challenge with Ascaris suum with both an acute bronchoconstriction and a late bronchial obstruction (W. M. Abraham, et al., Am. Rev. Resp. Dis., 128, 839-44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intobated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of RL from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L=R_L . V_{tg}$).

Aerosol Delivery Systems: Aerosols of Ascaris suum extract (1:20) are generated using a disposable medical nebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with Ascaris suum antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drag-treated animals.

PREPARATION OF BENZYL HALIDES

Halide 1: 3-[4-(4-Methoxy)tetrahydropyranyl]benzyl bromide

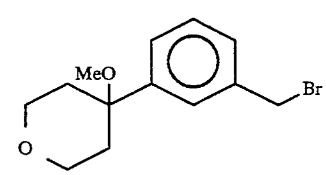

Step 1: 3-[4-(4-Hydroxy)tetrahydropyranyl]toluene

To a solution of 3-bromotoluene (24.3 mL; Aldrich) in THF (250 mL) stirred at −78° C. was added a solution of n-BuLi in hexane (1.75M; 114 mL; Aldrich). After 45 min., the resulting white suspension was treated with a solution of tetrahydropyran-4-one (18.5 mL; Aldrich) in THF (125 mL). After 45 min. at −78° C., the mixture was stirred for 1.5 hr. at r.t. Saturated aqueous $NH_4Cl$ was then added and the organic phase separated. The aqueous phase was extracted with EtOAc. The combined organic phases were washed with brine, dried ($MgSO_4$), and evaporated. Flash chromatography of the residue (silica gel; hexane/EtOAc (1:1)) followed by crystallization in hexane/EtOAc afforded the title compound as a white solid.

Step 2: 3-[4-(4-Methoxy)tetrahydropyranyl]toluene

To a 0° C. solution of the alcohol from Step 1 (38 g) in DMF (300 mL) were added Nail (60% in mineral oil; 16 g) and methyl iodide (31 mL). The mixture was stirred under nitrogen at r.t. for 15 hr. before $H_2O$ (1 L) was added. The aqueous phase was extracted with EtOAc and the combined organic phases were washed with brine, dried ($MgSO_4$), and evaporated. Flash chromatography of the residue (silica gel; hexane/EtOAc (4:1) yielded the title ether as a colorless liquid.

Step 3: 3-[4-(4-Methoxy)tetrahydropyranyl]benzyl bromide

A mixture of the toluene (16 g) from Step 2, N-bromosuccinimide (14.6 g) and azoisobutyronitrile (AIBN) (127 mg) in $CCl_4$ (250 mL) was refluxed for 1.5 hr. Filtration and evaporation of the filtrate gave the desired benzyl bromide.

Halide 2: 3-[4-(4-Hydroxy)tetrahydropyranyl]benzyl bromide

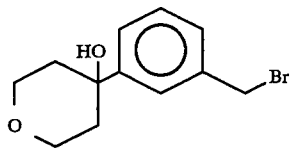

Following the procedure described for Halide 1, Step 3, but substituting 3-[4-(4-hydroxy)tetrahydropyranyl]-toluene (from Halide 1, Step 1) for 3-[4-(4-methoxy)tetrahydropyranyl]toluene, the title product was obtained as a yellow solid.

Halide 3: 3-[4-(4-Ethoxy)tetrahydropyranyl]benzyl chloride.

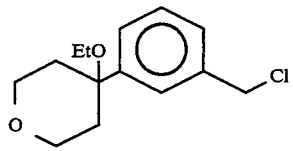

Step 1: 3-Bromobenzyl alcohol tetrahydropyranyl ether

A solution of 3-bromobenzyl alcohol (84.9 g; Aldrich), 3,4-dihydro-2H-pyran (44 g) and anhydrous p-toluene sulfonic acid (1 g) in $CH_2Cl_2$ (800 mL) was stirred at 5° C. for 1 hr then at r.t. overnight. The mixture was concentrated and the residue chromatographed (5% EtOAc/hexane) to afford the title compound as an oil.

Step 2: 3-[4-(4-Hydroxy)tetrahydropyranyl]benzyl alcohol tetrahydropyranyl ether Following the procedure described for Halide 1, Step 1, but substituting the bromo compound from Step 1 for 3-bromotoluene as starting material, the title compound was obtained as an oil.

Step 3: 3-[4-(4-Ethoxy)tetrahydropyranyl]benzyl alcohol tetrahydropyranyl ether To a solution of the alcohol (7.7 g) from Step 2 in DMF (50 mL) was added NaH (950 mg) in portions at r.t. After 1 hr, the mixture was cooled to 0° C. and ethyl iodide (3.16 mL) added. A further 1.5 mL ethyl iodide and 0.5 g NaH were added after 10 hr and the reaction left to stir overnight. The mixture was poured into water, extracted 3x ether, washed with brine, dried, and evaporated. Purification of the residue on silica gel (30% EtOAc/hexane as eluant) provided the title compound as an oil.

Step 4: 3-[4-(4-Ethoxy)tetrahydropyranyl]benzyl alcohol

To a solution of the tetrahydropyranyl ether from Step 3 (2.88 g) in MeOH (30 mL) at r.t. was added 3N HCl (15 mL) and the reaction stirred for 30 min. Ether was added to the mixture and the organic layer then washed with brine, dried and concentrated. Chromatography of the residue (40% EtOAc/hexane) afforded the title compound as an oil.

Step 5: 3-[4-(4-Ethoxy)tetrahydropyranyl]benzyl chloride

To a solution of the alcohol from Step 4 (1.78 g) and hexamethylphosphorous triamide (HMPT) in THF (35 mL) at 0° C. under nitrogen was added $CCl_4$ (1.5 mL) dropwise. After the addition was complete, the mixture was stirred for 5 min. before being concentrated vacuo. Chromatography of the residue (30% EtOAc/hexane) afforded the title compound as an oil.

Halide 4: 3-[4-(4-Cyclopropylmethoxy)tetrahydropyranyl]benzyl chloride

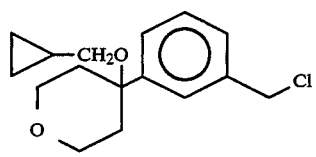

Following the procedure described for Halide 3, Steps 3–5, but substituting ethyl iodide for cyclopropyl methyl bromide (Aldrich) as starting material, the title compound was obtained as an oil.

Halide 5: 3-[4-(4β-Hydroxy-2,6-dimethyl)tetrahydropyranyl]benzyl bromide

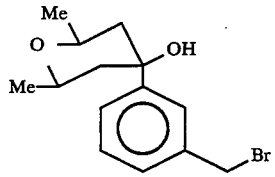

Step 1: 3-Bromo-O-tetrahydropyranylbenzyl alcohol

To a solution of 3-bromobenzyl alcohol (11.5 g; Aldrich) dissolved in $CH_2Cl_2$ (100 mL) at 0° C. and p-toluenesulfonic acid monohydrate (116 mg) was added DHP (6.2 mL). The resulting solution was stirred at r.t. for 3 hr. then was quenched with $NH_4OAc$. The aqueous phase was extracted with $CH_2Cl_2$. The combined organic phases were washed with brine, dried ($MgSO_4$), and evaporated. Flash chromatography of the residue (silica gel: hexane/EtOAc (9:1) afforded the title compound as an oil.

Step 2: 2,6-Dimethyltetrahydropyran-4-one

A solution of 2,6-dimethyl-γ-pyrone (17 g, Aldrich) in EtOH 95% (300 mL) was hydrogenated for 3 days under 70 psi. After filtration over celite, the solvent was evaporated and replaced by $CH_2Cl_2$. The solution was then treated with celite (30 g) and PCC (48.5 g). The suspension was stirred for 3 hr. and the reaction was diluted with $Et_2O$ (300 mL) and then filtered over a pad of celite. The filtrate was evaporated to dryness and the residual solution was then chromatographed using hexane/$Et_2O$ (1:1) to give the title compound.

Step 3:
3-[4-(4β-Hydroxy-2,6-dimethyl)tetrahydropyranyl]-O-tetrahydropyranylbenzyl alcohol Following the procedure described in Halide 1, Step 1, but substituting 3-bromo-O-tetrahydropyranylbenzyl alcohol (from Step 1) for 3-bromotoluene and substituting 2,6-dimethyltetrahydropyran-4-one (from Step 2) for tetrahydropyran-4-one, the title compound was obtained as a mixture of α and β isomers (30:70). Both isomers were isolated from a flash column (hexane/EtOAc) (6:4). The β-hydroxy isomer is more polar than the α-hydroxy isomer.

Step 4:
3-[4-(4β-Hydroxy-2,6-dimethyl)tetrahydropyranyl]benzyl alcohol

The β-hydroxy-THP derivative (1.0 g) from Step 3, was dissolved in EtOH (10 mL) and treated with p-toluenesulfonic acid (30 mg). The reaction was stirred at r.t. for 90 min. The EtOH was evaporated and the resulting syrup was flash chromatographed to give the title compound.

Step 5:
3-[4-(4β-Hydroxy-2,6-dimethyl)tetrahydropyranyl]benzyl bromide

To a solution of the alcohol (183 mg) from Step 4 in CH$_2$Cl$_2$ (9 mL) was added CBr$_4$ (269 mg). The reaction was then cooled to −30° C. and DIPHOS (298 mg) was added in portions. After 10 min., the reaction was quenched with a solution (10 mL) of 10% EtOAc in hexane and without evaporation, the solvent was poured onto a silica gel column and eluted with EtOAc/hexane (3:7) affording the title compound.

Halide 6:
3-[4-(4α-Hydroxy-2,6-dimethyl)tetrahydropyranyl]benzyl bromide

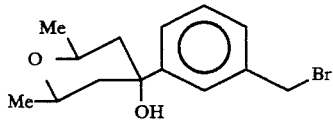

Following the procedure described in Halide 3, Steps 4–5, but substituting α-hydroxy-THP derivative (from Halide 3, Step 3) for β-hydroxy-THP derivative, the title product was obtained.

Halide 7:
4-Bromomethyl-2-[4-(4-hydroxy)tetrahydropyranyl]-thiazole

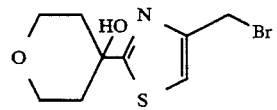

Step 1:
4-Methyl-2-[4-(4-hydroxy)tetrahydropyranyl]thiazole

To a solution of 4-methyl thiazole (990 mg) in THF (10 mL) at −78° C. there was added n-BuLi in hexanes (10 mL; 1.1M). The resulting suspension was stirred at −78° C. for 45 min. then there was added slowly a solution of tetrahydropyran-4-one (1.20 g) in THF (2 mL). The mixture was then stirred at 0° C. for 1 hr., then quenched with saturated aqueous NH$_4$Cl (8 mL), and diluted with EtOAc. The organic phase was washed (3x) with brine, dried and evaporated to a residue which was chromatographed on silica gel, eluting with a 1:1 mixture of EtOAc and hexane to afford the product as a light yellow solid.

Step 2:
4-Bromomethyl-2-[4-(4-hydroxy)tetrahydropyranyl]-thiazole

Following the procedure described in Halide 1, Step 3, but substituting 4-methyl-2-[4-(4-hydroxy)tetrahydropyranyl]thiazole from Step 1, for 3-[4-(4-methoxy)-tetrahydropyranyl]toluene, the title product was obtained as a white solid.

Halide 8:
3-[4-(2,2-Dimethyl-4-ethyl-1,3-dioxolanyl)]benzyl bromide

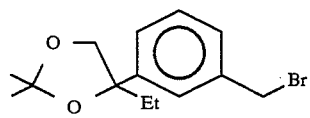

Step 1: 3-Methylpropiophenone

To a 0° C. solution of EtMgBr in Et$_2$O (3.0M, 570 mL, Aldrich) was slowly added m-tolunitrile (102 mL, Aldrich). After stirring at r.t. for 19 hr., benzene (300 mL) was added and the resulting mixture was cooled to 0° C. HCl (6N, 600 mL) was then slowly added. The organic phase was separated, washed with 5% NaHCO$_3$ and brine, dried (MgSO$_4$), and evaporated to afford the desired ketone as a yellow liquid.

Step 2:
3-[2-(1-Isopropoxydimethylsilylbutan-2-ol)]toluene

A solution of the ketone from Step 1 (2.5 g) in THF (15 mL) was added dropwise to a 0° C. solution of isopropoxydimethylsilylmethylmagnesium chloride (5.6 mmoL, J. Org. Chem., 1983, 48, 2120) in THF (10 mL). The mixture was stirred at r.t. under argon for 2 hr. before it was washed with saturated NH$_4$Cl solution and brine, dried (MgSO4), and evaporated. Flash chromatography of the residue (silica gel; hexane/EtOAc (95:5)) yielded the title alcohol as a colorless oil.

Step 3: 3-[2-(Butan-1,2-diol)]toluene

A mixture of the alcohol from Step 2 (3.67 g), THF (20 mL), MeOH (20 mL), NaHCO$_3$ (1.25 g), and H$_2$O$_2$ (30%) (12.8 mL) was refluxed for 3 hr. After evaporation, the residue was taken up in EtOAc and the organic phase was washed with brine, dried (MgSO$_4$) and evaporated. Flash chromatography of the residue (silica gel; hexane/EtOAc (3:2)) yielded the desired diol as a colorless oil.

Step 4:
3-[4-(2,2-Dimethyl-4-ethyl-1,3-dioxolanyl)]toluene

Concentrated sulphuric acid (1 drop) was added to a solution of the diol from Step 3 (1.0 g) in acetone (50 mL). The reaction mixture was stirred for 2 hr. at r.t. before it was neutralized by the addition of 1N NaOH and evaporated. Flash chromatography of the residue

Step 5: 3-[4-(2,2-Dimethyl-4-ethyl-1,3-dioxolanyl)]benzyl bromide

Following the procedure described in Halide 1, Step 3, but substituting the toluene from Step 4 for 3-[4-(4-methoxy)tetrahydropyranyl]toluene, the title benzyl bromide was obtained as an oil.

Halide 9.: 7-Bromomethyl-4-(3-furyl)coumarin

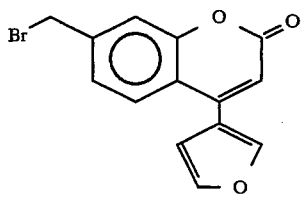

Step 1: 7-Methylcoumarin-4-yl trifluoromethanesulfonate

To a solution of 4-hydroxy-7-methylcoumarin (2.17 g, 12.3 mmol) (Anschütz et al., Liebigs Ann. Chem. 1909, 367, 219) in 20 mL $CH_2Cl_2$ at 0° C. was added $Et_3N$ (1.48 g, 14.8 mmol) and trifluoromethanesulfonic anhydride (4.18 g, 14.8 mmol). The mixture was stirred for 2.5 h. at 0° C., then 50 mL of hexane/$Et_2O$ (1:1) was added. The solvent was evaporated and the residue chromatographed over silica gel using 30% EtOAc in hexane as eluant to give 2.8 g (74%) of the title compound as a white solid, m.p. 95°–96° C.

Step 2: 4-(3-furyl)-7-methylcoumarin

To a solution of 3-bromofuran (2.36 g, 16.1 mmol) in dry $Et_2O$ (146 ml) was added at −78° C. n-BuLi in hexane (6.42 ml, 16.1 mmol, 2.5M). The resulting solution was stirred for 20 min., then $(MeO)_3B$ (1.82 ml, 16.1 mmol) was added dropwise and after 20 min., a mixture of the triflate from Step 1 (4.50 g, 14.6 mmol) and $(PPh_3)_4Pd$ (1.69 g, 1.46 mmol) in THF (60 ml) and $H_2O$ (10 ml) was added. The cooling bath was removed and the resulting mixture was heated to 65° C. for 1.75 h. The solvent was evaporated and $H_2O$ was added followed by extraction with EtOAc (3×50 ml). The combined organic phases were washed with brine, dried over $MgSO_4$ and evaporated. Purification by flash chromatography (toluene: (2–10% EtOAc)) gave 2.5 g of the title compound, m.p. 160°–162° C.

Step 3: 7-Bromomethyl-4-(3-furyl)coumarin

N-Bromosuccinimide (0.90 g, 5.06 mmol) was added to a stirred solution of the compound from Step 2 (1.04 g, 4.60 mmol) in $CCl_4$ (150 ml) followed by a catalytic amount of azobis (isobutyronitrile). After the mixture was refluxed for 3 h., the precipitated solid was removed by filtration and the solvent was evaporated in vacuo. The residue was stirred for 10 min. in 15 ml $Et_2O$, filtered and dried to give 0.69 g of the title compound, m.p. 155°–156° C.

PREPARATION OF ALCOHOLS

Alcohol 1: 3-[4-(4-Hydroxy)tetrahydropyranyl]benzyl alcohol

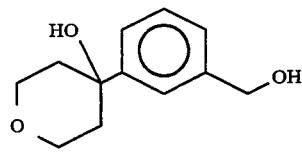

Step 1: 3-Bromo-O-tert-butyldiphenylsilylbenzyl alcohol

To a solution of 3-bromobenzyl alcohol (25 g, 134 mmoL) in anhydrous DMF (300 mL) was added triethylamine (17.6 g, 174 mmoL) followed by t-butyldiphenylsilyl chloride (40.4 g, 147 mmoL). The mixture was stirred for 24 hr, poured into a saturated aqueous $NH_4Cl$ solution (1 L), and extracted with $Et_2O$. The combined organic layers were washed with brine, dried over $MgSO_4$, and evaporated. Flash chromatography on silica gel (2.5% EtOAc in hexane) afforded the title compound as a colorless oil.

Step 2: 3-[4-(4-Hydroxy)tetrahydropyranyl]benzyl alcohol

Following the procedure described in Halide 1, Step 1, but substituting 3-bromo-O-tert-butyldiphenylsilylbenzyl alcohol (from Step 1) for 3-bromotoluene, the tert-butyldiphenylsilylether derivative of the title compound was obtained. The crude product was treated with 5 equivalents of $Bu_4NF$ in dry THF at r.t. for 1.5 hr. After evaporation of the solvent, the crude product was flash chromatographed on silica gel (toluene:EtOAc/1:4) to afford the pure title compound as a colorless oil.

Alcohols 2 and 3: 3-[4-(4α-Hydroxy-2-methyl)tetrahydropyranyl]benzyl alcohol (2) and 3-[4-(4β-hydroxy-2-methyl)tetrahydropyranyl]benzyl alcohol (3)

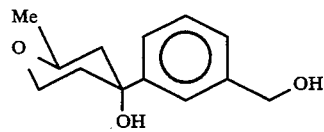

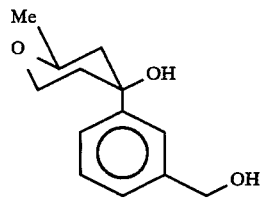

Following the procedure in Halide 1, Step 1, but substituting 3-bromo-O-tert-butyldiphenylsilylbenzyl alcohol (from Alcohol 1, Step 1) for 3-bromotoluene and substituting 2-methyl-tetrahydropyran-4-one (Jour. Amer. Chem. Soc., 1982, 104, 4666) for tetrahydropyran-4-one. The tert-butyldiphenylsilylether derivatives of the title compounds were obtained as a mixture of α- and β-isomers. This mixture was then treated with 5 equivalents of Bu₄NF in dry THF at r.t. for 1.5 hr. After evaporation of the solvent both isomers were separated by using flash chromatography (toluene:EtOAc/1:4) affording firstly the α-hydroxy isomer (Alcohol 2) followed by the β-isomer (Alcohol 3) in a ratio 1:2.8, respectively.

Alcohol 4:
[1S,5R]3-[3-(3α-Hydroxy-6,8-dioxabicyclo[3.2.1 ]octanyl)]benzyl alcohol

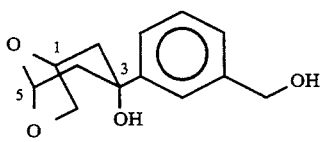

Step 1: 2,4-Di-O-p-toluenesulfonyl-1,6-anhydro-β-D-glucose

To a solution of 1,6-anhydro-β-D-glucose (50 g, 308 mmoL) in dry pyridine (100 mL) at 0° C. was added dropwise a solution of p-toluenesulfonyl chloride (123 g, 647 mmoL) dissolved in CHCl₃ (350 mL) and pyridine (200 mL). The reaction mixture was stirred at r.t. for 2 days. Water was added and the reaction mixture was stirred for ~1 hr, then the organic layer was decanted and the aqueous phase was reextracted with CHCl₃. The combined organic layers were washed with H₂SO₄ (10%) until the pH remained acidic, then finally washed with a saturated NH₄OAc solution. The resulting organic layer was dried over MgSO₄ and the solvent evaporated. The syrup obtained was flash chromatographed on silica gel eluting with hexane:EtOAc (1:1) to give the title compound an oil.

Step 2: [1 S,3S,5R]6,8-Dioxabicyclo[3.2.1]octan-3-one

The ditosylate derivative from Step 1 (107 g, 0.228 mmoL) was dissolved in THF (1.6 L) at −40° C. and Super-Hydride® in THF (800 mL, 1M, 0.8 mmoL) was slowly added. The resulting reaction mixture was stirred at r.t. overnight. The reaction was cannulated into cold H₂O (226 mL) using external cooling, then NaOH 3N (640 mL, 1.92 mmol) and H₂O₂ (30%) (490 mL, 4.3 mmol) were successively added. The reaction was stirred at r.t. for 1 hr, then the supernatant (THF layer) was separated from the aqueous layer and concentrated. The resulting residue was combined with the aqueous layer and extracted with CH₂Cl₂ using a continuous extractor. The organic layer was dried (MgSO₄) and evaporated to dryness. The oily residue was dissolved in hot Et₂O, filtered and evaporated to dryness affording the title compound contaminated with the 2-octanol isomer. The crude product was used as such for the next step.

Step 3: [1S,5R]6,8-dioxabicyclo[3.2.1]octan-3-one

The crude alcohol from Step 2 (16.6 g, 89 mmoL) in CH₂Cl₂ (200 mL) was added slowly to a suspension of PCC (38.4 g, 178 mmoL) and celite (22 g) in CH₂Cl₂ (400 mL) and stirred for 1 hr. The reaction mixture was diluted with Et₂O (600 mL) and filtered over celite. The filtrate was evaporated and the residue distilled with a Kügelrohr apparatus (100° C., 1.8 mm/Hg) affording the title product as an oil.

Step 4: [1S,5R]3-[3-(3α-Hydroxy-6,8-dioxabicyclo[3,2,1 ]octanyl]benzyl alcohol

Following the procedure described in Halide, Step 1, but substituting 3-bromo-O-tert-butyldiphenylsilylbenzyl alcohol (from Alcohol 1, Step 1) for 3-bromotoluene, the tert-butyldiphenylsilylether derivative of the title compound was obtained. The crude product was treated with 1 equivalent of Bu₄NF in dry THF at r.t. for 1.5 hr. After evaporation of the solvent, the crude product was flash chromato-graphed on silica gel (hexane:EtOAc/4:1) to afford the pure title product as a colorless oil.

Alcohol 5:
5-[4-(4-Hydroxy)tetrahydropyranyl]pyridin-3-ylmethanol

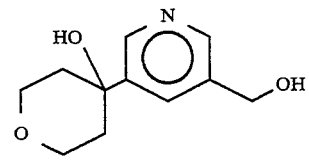

Step 1:
5-Bromo-0-tert-butyldiphenylsilylpyridin-3-ylmethanol

To a solution of 5-bromopyridin-3-ylmethanol (Chem. Pharm. Bull. 1990, 38, 2446) (29 g, 154 mmoL) and tert-butylchlorodiphenylsilane (47.5 g, 173 mmoL) in CH₂Cl₂ (500 mL) at r.t., there was added imidazole (15.8 g, 232 mmoL). The mixture was stirred for 1 hr. and filtered. The filtrate was evaporated and the residue chromatographed on silica gel, eluting with a 1:7 mixture of EtOAc and hexane, to afford the product as a colorless oil.

Step 2:
5-[4-(4-Hydroxy)tetrahydropyranyl]-0-tert-butyldiphenylsilylpyridin-3-ylmethanol To a solution of the silylether from Step 1 (50 g, 117 mmoL) in THF (500 mL), cooled to −70° C., there was slowly added n-BuLi in hexanes (115 mL, 129 mmoL, 1.12M) affording a dark brown solution. To this, there was added a solution of tetrahydro-4H-pyran-4-one (14.1 g, 141 mmoL) in THF (925 mL). The resulting mixture was stirred for 1 hr. at −70° C., then quenched slowly with saturated aqueous NH₄Cl (50 mL) and allowed to warm up to r.t. After diluting with EtOAc (500 mL) the mixture was washed (4x) with brine, dried over Na₂SO₄ and evaporated. Chromatography on silica gel, eluting with EtOAc, afforded the product as an oil which solidified.

Step 3:
5-[4-(4-Hydroxy)tetrahydropyranyl]pyridin-3-ylmethanol

To a solution of the silylether from Step 2 (20.35 g, 45.5 mmoL) in THF (350 mL), there was added Bu₄NF in THF (52 mL, 1M) and the mixture was stirred at r.t. for 1 hr. The solvent was evaporated and the residue chromatographed as a short column of silica gel, eluting with a 1:4 mixture of EtOH and EtOAc, to afford the title product which was obtained, after trituration with Et₂O and filtration, as a light yellow solid, m.p. 145°-147° C.

Alcohol 6:
6-[4-(4-Hydroxy)tetrahydropyranyl]pyridin-2-ylmethanol

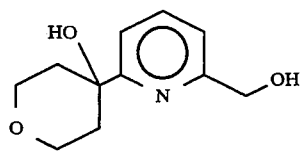

Step 1:
2-Bromo-6-[4-(4-hydroxy)tetrahydropyranyl]pyridine

A solution of 2,6-dibromopyridine (15 g) in Et$_2$O (375 mL) was cooled to −78° C. To the resulting suspension was slowly added n-BuLi in hexanes (47.5 mL, 2M, 0.9 eq.) and the resulting mixture was stirred for a further 15 min. at −78° C. There was slowly added a solution of tetrahydro-4H-pyran-4-one (11.6 g) in Et$_2$O (25 mL). The resulting white suspension was stirred at −78° C. for an additional 15 min. There was added saturated aqueous NH$_4$Cl (100 mL) and the mixture was allowed to warm up to r.t. After dilution with EtOAc, the organic phase was washed (4x) with brine, dried and evaporated. The residue was triturated with Et$_2$O and filtered to afford the title product as a white solid, m.p. 131°–133° C.

Step 2:
6-[4-(4-Hydroxy)tetrahydropyranyl]pyridin-2-ylmethanol

To a solution of the bromo derivative from Step 1 (7.7 g) in THF (50 mL) and Et$_2$O (150 mL), cooled to 0° C., there was slowly added n-BuLi in hexanes (30 mL, 2M) affording a red-brown suspension. An inlet tube above the surface of the mixture was connected to a flask in which paraformaldehyde (25 g) was gently heated at 175° C. to generate formaldehyde. When all the paraformaldehyde had been decomposed, to the reaction mixture was added saturated aqueous NH$_4$Cl (100 mL) and EtOAc (500 mL). The organic phase was washed (4x) with b rine, dried and evaporated to a residue which was chromatographed on silica gel, eluting with EtOAc to afford the title product as a thick yellow oil.

Alcohol 7:
6-[4-(4-Methoxy)tetrahydropyranyl]pyridin-2-ylmethanol

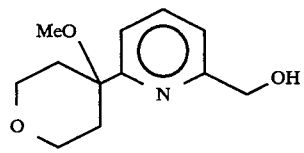

Step 1:
2-Bromo-6-[4-(4-methoxy)tetrahydropyranyl]pyridine

To a suspension of KH (35% dispersion in oil, 1.25 g) in THF (75 mL), cooled to 0° C., there was added 2-bromo-6-[4-(4-hydroxy)tetrahydropyranyl]pyridine from Alcohol 6, Step 1. When gassing had subsided, the mixture was warmed to r.t. and a thick suspension resulted. To this was added methyl iodide (1.71 g) and the resulting suspension was stirred at r.t. for 30 min. The THF was evaporated away, and the residue was partitioned between H$_2$O and EtOAc. The residue from evaporation of the organic phase was triturated with hexane and filtered to afford the product as a white solid, m.p. 69°–71° C.

Step 2:
6-[4(4-Methoxy)tetrahydropyranyl]pyridin-2-ylmethanol

Following the procedure described in Alcohol 6, Step 2, but substituting the bromo derivative from Step 1 for 2-bromo-6-[4-(4hydroxy)tetrahydropyranyl]pyridine, the title product was obtained as a white solid, m.p. 84°–86° C.

Alcohol 8:
4-[4-(4-Hydroxy)tetrahydropyranyl]pyridin-2-ylmethanol

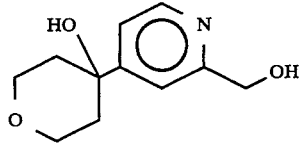

Following the procedure described in Alcohol 5, Steps 1–3, but substituting 4-bromopyridin-2-ylmethanol (Chem. Pharm. Bull. 1990, 38, 2446) for 5-bromo-pyridin-3-ylmethanol as starting material, the title product was obtained as a white solid.

Alcohol 9:
[1S,5R]5-[3-(3α-Hydroxy-6,8-dioxabicyclo[3.2.1]octanyl)]pyridin-3-ylmethanol

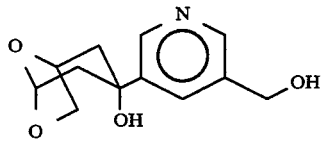

Following the procedure described in Alcohol 5, Steps 2–3, but substituting [1S,5R]6,8-dioxabicyclo[3.2.-1]octan-4-one from Alcohol 4, Step 3 for tetrahydro-4H-pyran-4-one, the title product was obtained as a white solid.

Alcohol 10:
[1S,5R]6-[3-(3α-Hydroxy-6,8-dioxabicyclo[3.2.1]octanyl)]pyridin-2-ylmethanol

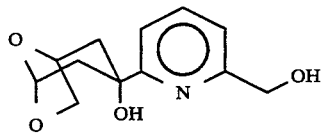

Step 1:
6-Bromo-O-tert-butyldiphenylsilylpyridin-2-ylmethanol

Following the procedure described in Alcohol 5, Step 1, but substituting 6-bromopyridin-2-ylmethanol (Chem. Pharm. Bull. 1990, 38, 2446) for 5-bromopyridin-3-ylmethanol, the title product was obtained as a colorless oil.

Step 2:
[1S,5R]6-[3-(3α-Hydroxy-6,8-dioxabicyclo[3.2.1]octanyl)]pyridin-2-ylmethanol Following the procedure described in Alcohol 5, Steps 2–3, but substituting 6-bromo-O-tert-butyldiphenylsilylpyridin-2-yl-methanol from Step 1, for 5-bromo-O-tert-butyldiphenylsilylpyridin-3-ylmethanol and substituting [1S,5R]6,8-dioxabicyclo[3.2.1]octan-4-one from Alcohol 4, Step 3, for tetrahydro-4H-pyran-4-one, the title product was obtained as a white solid.

Alcohol 11:
3-Fluoro-5-[4-(4-hydroxy)tetrahydropyranyl]-phenol

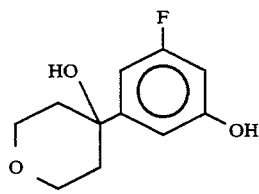

The title alcohol was prepared according to the procedure given in J. Med. Chem., 1992, 35, 2600–2609.

Alcohols 12–15 were prepared from [1S,5R]6,8-dioxabicyclo[3.2.1]-octan-3-one (from Alcohol 4, Step 3) and either 3-benzyloxyphenyl bromide or 5-benzyloxy-3-fluorophenyl bromide using the procedures given in J. Med. Chem, 1992, 35, 2600–2609.

Alcohol 12:
[1S,5R]3-Fluoro-5-[3-(3α-hydroxy-6,8-dioxabicyclo[3.2.1]octanyl)phenol

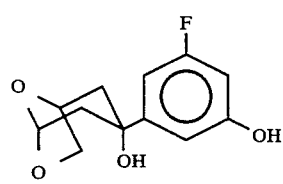

Alcohol 13:
[1S,5R]3-Fluoro-5-[3-(3α-methoxy-6,8-dioxabicyclo[3.2.1]octanyl)]phenol

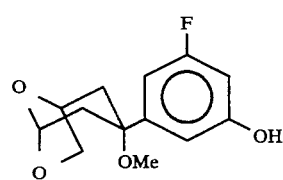

Alcohol 14:
[1S,5R]3-[3-(3α-hydroxy-6,8-dioxabicyclo[3.2.1]octanyl)]phenol

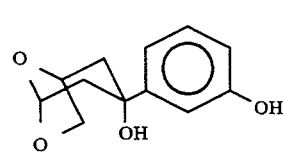

Alcohol 15:
[1S,5R]3-[3-(3α-Methoxy-6,8-dioxabicyclo[3.2.1]octanyl)]phenol

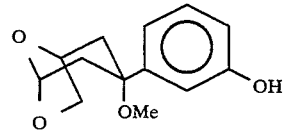

Alcohol 16: (+)3-Fluoro-5-[3(3α-hydroxy-5-methyl-6,8-dioxabicyclo[3.2.1]octanyl)]phenol

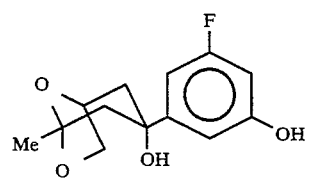

Step 1: 2-Benzyloxy acetaldehyde

A solution of 11.1 g of 1,4-bis(benzyloxy)-2-butene (Garner, et al., Synthetic Communications, 17 #2 p. 184 (1987)) in a mixture of 400 mL of CH$_2$Cl$_2$ and 100 mL of MeOH containing 2.6 g NaHCO$_3$, was cooled to −78° C. Ozone was passed into the mixture until the blue color persisted. Nitrogen was then bubbled through to remove the excess of ozone and dimethyl sulfide (1.3 eq.) was added. After warming to r.t. and stirring overnight, the reaction was filtered and concentrated. To the residual syrup was added 34 mL of H$_2$O and 12 mL of HOAc followed by 8.0 g of Zn dust. After stirring vigorously for 60 min., the mixture was filtered and the residue was washed 3x with Et$_2$O. The filtrate was extracted with Et$_2$O and the organic layer was washed with brine and saturated aqueous NaHCO$_3$, then dried with MgSO$_4$. It was concentrated in vacuo to give 15 g of syrup. The residue was purified by flash chromatography on 200 g of silica gel with 15% ether/pentane to give 10.8 g of the title product (87%).

Step 2:
6-Benzyloxymethyl-2-methyl-5,6-dihydro-4H-pyran-4-one

A solution of 10.4 g of the aldehyde from Step 1 in 250 ml of THF was cooled to 0° C. and 1.0 eq. of freshly prepared MgBr$_2$ was added dropwise. The mixture was warmed to r.t. and 40.6 g of 1,3-bis(trimethylsilyloxy)-1,3-butadiene (Emde, et al., Synthesis, p. 6 (1982)) was added. After 3 h., 50% aqueous HOAc was added and the mixture was stirred 10 min. and then extracted with Et$_2$O (2x). After the ether was evaporated, the resultant oil was taken back up in 300 ml of CH$_2$Cl$_2$ and 12 ml of TFA. After 3 hours, the solution was washed with H$_2$O, saturated NaHCO$_3$, brine and finally dried over MgSO$_4$. After flash chromatography, 9.5 g (60%) of the title compound was obtained.

Step 3: 5.-Methyl-3-oxo-6,8-dioxabicyclo[3.2.1]octane

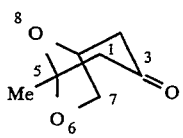

A solution of 4.4 g of the 6-Benzyloxy compound from Step 2 in EtOAc was hydrogenated with H₂ and Pd/C (10%). After completion, the reaction was filtrated on a bed of celite and then evaporated to dryness. The cru syrup was then taken up in CH₂Cl₂ containing 1 g of camphor sulphonic acid. The reaction was stirred at r.t. overnight, filtered and evaporated. Purification by flash chromatography (30% Et₂O/pentane) gave 780 mg of the title compound (30%).

Step 4: (+) 3-Fluoro-5-[3-(3α-hydroxy-5-methyl-6,8-dioxabicyclo[3.2.1]octanyl)]phenol Using the procedures given in J. Med. Chem., 1992, 35, 2600–2609, the title compound was prepared from the ketone of Step 3.

The invention is illustrated by the following non-limiting examples in which, unless stated otherwise:

(i) all operations were carried out at room or ambient temperature, that is, at a temperature in the range 18°–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and "d" indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry, or microanalytical data;

(vi) yields are given for illustration only;

(vii) when given, NMR data are in the form of delta (δ) values for major diagnostic protons, given in parts per million (ppm) relative to tetramethylsilane (TMS) as internal standard, determined at 250 MHz or 300 MHz using the indicated solvent; conventional abbreviations used for signal shape are: s. singlet; d. doublet; t. triplet; m. multiplet; br. broad; etc.; in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

3-{4-[3-(4-(4-Methoxy)tetrahydropyranyl)benzyloxy)]-2-hydroxyphenyl}propenoic acid disodium salt.

Step 1:
7-[3-(4-(4-Methoxy)tetrahydropyranyl)benzyloxy]-coumarin

A solution of 7-hydroxycoumarin (Aldrich; 370 mg), 3-[4-(4-methoxy)tetrahydropyranyl]benzyl bromide (843 mg) and Cs₂CO₃ (1.12 g) in DMF was stirred at 60° C. under nitrogen for 4 hr. The mixture was cooled, poured onto 1N HCl, extracted (3x EtOAc), washed twice with brine, dried, and evaporated. Crystallisation of the resulting oil from ether and filtration provided the title compound as a solid, m.p. 103.5°–105.5° C.

Step 2:
3-{4-[3-(4-(4-Methoxy)tetrahydropyranyl)benzyloxy)]-2-hydroxy-phenyl}propenoic acid disodium salt A solution of the lactone from Step 1 in THF is treated with 2 equivalents of 1N NaOH and the mixture heated at reflux for 2 hr. The solvent is removed in vacuo and the residue is azeotroped twice with EtOAc/toluene to afford the title compound.

EXAMPLE 2

3-Methyl-3-{4-[3-(4-(4-methoxy)tetrahydropyranyl)-benzyloxy]-2-hydroxyphenyl}propenoic acid disodium salt Following the procedure described for Example 1, Steps 1 and 2, but substituting 7-hydroxycoumarin with 7-hydroxy-4-methylcoumarin (Aldrich) as starting material in Step 1, the title compound is obtained.

EXAMPLE 3

3-Methyl-3-{4-[3-(4-(4-methoxy)tetrahydropyranyl)-benzyloxy]-2-hydroxy-6-chlorophenyl}propenoic acid disodium salt Following the procedure described for Example 1, Steps 1 and 2, but substituting 7-hydroxycoumarin with 6-chloro-7-hydroxy-4-methyl-coumarin (Chem. Abst. 81: 49519n (1974)) as starting material in Step 1, the title product is obtained.

EXAMPLE 4

3-(Prop-1-yl)-3-{4-[3-(4-(4-methoxy)tetrahydropyranyl)benzyloxy]-2-hydroxyphenyl}propenoic acid disodium salt Step 1: 4-Butyryl-1,3-dihydroxybenzene To a solution of resorcinol (1.5 g) and butyric acid (2.9 mL) in 1,2-dichloroethane (45 mL) was added ZnCl₂ (3.22 g) and the mixture then heated at 150° C. under nitrogen for 5 hr. The reaction mixture was cooled, poured onto 1N HCl/brine and extracted (3x EtOAc). After washing with 0.1N K₂CO₃, then twice with brine, the organic layer was dried and evaporated. Chromatography of the residue (silica gel; hexane/EtOAc 2:1) afforded the title product as a solid.

Step 2:
1-[3-(4-(4-Methoxy)tetrahydropyranyl)benzyloxy]-3-hydroxy-4-butyrylbenzene A mixture of the diphenol from Step 1 (500 mg), 3-[4-(4methoxy)tetrahydropyranyl]benzyl bromide (950 mg) and Cs₂CO₃ (1.0 g) in DMF (15 mL) were stirred at r.t. for 5 hr. The solution was poured onto 1N HCl, extracted (3x EtOAc), washed twice with brine, dried and evaporated. The residue was chromatographed (hexane/EtOAc 3:1) to afford the title compound as a solid.

Step 3:
7-[3-(4-(4-Methoxy)tetrahydropyranyl)benzyloxy]-4-propylcoumarin

The ketophenol from Step 2 (590 mg) and methyl (triphenylphosphoranylidene) acetate (2.0 g) were heated at reflux in toluene (10 mL) overnight. After removal of the solvent, ether/hexane was added and the mixture filtered. The filtrate was evaporated, the residue chromatographed (hexane/EtOAc 2:1) and the product crystallised from ether/hexane 1:2. Filtration afforded the title compound as a solid, m.p. 115°–116° C.

Step 4:
3-(Prop-1-yl)-3-{4-[3-(4-(4-methoxy)tetrahydropyranyl)benzyloxy]-2-hydroxy-phenyl}propenoic acid disodium salt Following the procedure described in Example 1, Step 2, but substituting the coumarin from Step 3 for 7-[3-(4-(4-methoxy)tetrahydropyranyl)benzyloxy]-coumarin as starting material, the title compound is obtained.

EXAMPLE 5

3-Phenyl-3-{4-[3-(4-(4-hydroxy)tetrahydropyranyl)benzyloxy]-2-hydroxyphenyl}propenoic acid disodium salt Step 1: 4-[3-(4-(4-Hydroxy)tetrahydropyranyl)benzyloxy]-2-hydroxybenzophenone A mixture of 2,4-dihydroxybenzophenone (Aldrich; 1.0 g), 3-(4-(4-hydroxy)tetrahydropyranyl)benzyl bromide (1.5 g) and $Cs_2CO_3$ (1.83 g) in DMF (25 mL) were stirred at r.t. for 3 hr. The reaction mixture was poured onto water, extracted (3x EtOAc), washed twice with brine, dried and evaporated. Chromatography of the residue (hexane/EtOAc 1:1) afforded the title compound as a solid.

Step 2:
7-[3-(4-(4-Hydroxy)tetrahydropyranyl)benzyloxy]-4-phenylcoumarin

The ketophenol from Step 1 (1.6 g) and methyl (triphenylphosphoranylidene) acetate (5.0 g) were heated to reflux in toluene (20 mL) overnight. After removal of the solvent, ether was added and the mixture filtered. The filtrate was evaporated and the residue chromatographed (hexane/EtOAc 1:1) to afford the title product as a foam; m/e required for $C_{27}H_{24}O_5$: 428; found: 428.

Step 3:
3-Phenyl-3-{4-[3-(4-(4-hydroxy)tetrahydropyranyl)benzyloxy]-2-hydroxyphenyl}propenoic acid disodium salt Following the procedure described in Example 1, Step 2, but substituting the coumarin from Step 2 for 7-[3-(4-(4-methoxy)tetrahydropyranyl)benzyloxy]-coumarin as starting material, the title compound was obtained.

$^1$H NMR ($d^6$DMSO): δ 5 1.55 (2H, m), 1.95 (2H, m), 3.6–3.9 (4H, m), 4.89 (2H, s), 5.16 (1H, s), 5.75 (1H, bs), 6.05 (1H, bs), 6.16 (1H, s), 6.37 (1H, d, J=7.3 Hz), 7.05–7.6 (9H, m).

EXAMPLE 6

3-Phenyl-3-{4-[3-(4-(4-methoxy)tetrahydropyranyl)-benzyloxy]-2-hydroxyphenyl}propenoic acid disodium salt

Step 1:
7-[3-(4-(4-Methoxy)tetrahydropyranyl)benzyloxy]-4-phenylcoumarin

Following the procedure described for Example 5, Steps 1 and 2, but substituting 3-(4-(4-hydroxy)tetrahydropyranyl)benzyl bromide with 3-(4-(4-methoxy)tetrahydropyranyl)benzyl bromide as starting material in Step 1, the title compound was obtained as a solid, m.p. 123.5°–124.5° C.

Step 2:
3-Phenyl-3-{4-[3-(4-(4-methoxy)tetrahydropyranyl)-benzyloxy]-2-hydroxyphenyl}propenoic acid disodium salt Following the procedure described in Example 1, Step 2, but substituting the coumarin from Step 1 for 7-[3-(4-(4-methoxy)tetrahydropyranyl)benzyloxy]-coumarin as starting material, the title compound was obtained.

$^1$H NMR ($d^6$DMSO): δ 1.9 (4H, m), 2.87 (3H, s), 3.68 (4H, m), 4.92 (2H, s), 5.77 (1H, bs), 6.05 (1H, bs), 6.17 (1H, s), 6.38 (1H, d, J=7.3 Hz), 7.05–7.50 (9H, m).

EXAMPLE 7

3-(3-Furyl)-3-{4-[3-(4-(4-hydroxy)tetrahydropyranyl)-benzyloxy]-2-hydroxypheny}propenoic acid disodium salt Step 1: 4-(3-Furyl)-7-hydroxycoumarin A mixture of ethyl 3-oxo-3-(3-furyl)propionate (Aldrich; 3.17 g) and resorcinol (3.83 g) was treated with polyphosphoric acid (15 g) and heated to 110° C. under nitrogen. After 2 hr, the tarry mixture was cooled, then $H_2O$ and THF were added until a solution was obtained. Brine and EtOAc were added, the organic layer was removed and washed twice with brine. Chromatography of the residue, after concentration, using hexane/EtOAc 2:1 followed by swishing the product with ether afforded the title compound as a solid, m.p. 229°–232° C.

Step 2:
7-[3-(4-(4-Hydroxy)tetrahydropyranyl)benzyloxy]-4-(3-furyl)coumarin

Following the procedure described for Example 1 but substituting the phenol from Step 1 for 7-hydroxycoumarin and 3-[4-(4-hydroxy)tetrahydropyranyl]benzyl bromide for 3-[4-(4-methoxy)tetrahydropyranyl]benzyl bromide, the title compound was obtained as a foam.

$^1$H NMR (CDCl$_3$); δ 1.6 (m, 2H), 2.2 (m, 2H), 3.9 (m, 4H), 5.15 (s, 2H), 6.28 (s, 1H), 6.68 (s, 1H), 6.95 (m, 2H), 7.4 (m, 6H) and 7.8 (s, 1H).

Step 3:
3-(3-Furyl)-3-{4-[3-(4-(4-hydroxy)tetrahydropyranyl)-benzyloxy]-2-hydroxypheny}propenoic acid disodium salt Following the procedure described in Example 1, Step 2, but substituting the coumarin from Step 2 for 7-[3-(4-(4-methoxy)tetrahydropyranyl)benzyloxy]- coumarin as starting material, the title compound is obtained.

EXAMPLE 8

3-(3-Furyl)-3-{4-[3-(4-(4-methoxy)tetrahydropyranyl)-benzyloxy]-2-hydroxyphenyl}propenoic acid disodium salt Following the procedure described for Example 1, Steps 1-2, but substituting 7-hydroxycoumarin with 4-(3-furyl)-7-hydroxy-coumarin (from Example 7, Step 1) as starting material in Step 1, the title compound was obtained as a solid.

$^1$H NMR (d$^6$ DMSO): δ 1.8-2.05 (m, 4H), 2.85 (s, 3H), 3.55-3.80 (m, 4H), 4.8 (s, 2H), 5.7-6.3 (m, 2H), 6.45-6.75 (m, 2H), 7.0 (s, 1H), 7.15-7.6 (m, 6H).

EXAMPLE 9

3-(3-Thienyl)-3-{4-[3-(4-(4-hydroxy)tetrahydropyranyl)benzyloxy]-2-hydroxyphenyl}propenoic acid disodium salt

Step 1: 3-Thiophenecarbonyl chloride

3-Thiophenecarboxylic acid (Aldrich; 2.56 g), dichloromethyl methyl ether (2.4 mL) and ZnCl$_2$ (2 crystals) were heated at 100° C. for 30 min., under nitrogen. The excess reagent was removed in vacuo and the crude acid chloride was used as such in the next step.

Step 2: Ethyl 3-oxo-3-(3-thienyl)propionate

To a solution of N-isopropylcyclohexylamine (5.64 g) in THF (80 mL) cooled to −78° C. under nitrogen was added nBuLi (25 mL, 1.6M in hexane) and the mixture was stirred for 30 min. EtOAc (1.95 mL) was added and after a further 30 min., 3-thiophene carbonyl chloride (from Step 1) dissolved in 3 mL THF was added. After 30 min., 1N HCl (75 mL) was added followed by brine and EtOAc. The organic layer was separated, dried and concentrated. Purification by column chromatography (5% EtOAc/hexane) afforded the title compound as an oil.

Step 3: 7-Hydroxy4-(3-thienyl)coumarin

Following the procedure described in Example 7, Step 1, but substituting ethyl 3-oxo-3-(3-furyl)propionate with ethyl 3-oxo-3-(3-thienyl)propionate (from Step 2) as starting material, the title compound was obtained as a solid, m.p. 234°-236° C.

Step 4: 7-[3-(4-(4-Hydroxy)tetrahydropyranyl)benzyloxy]-4-(3-thienyl)coumarin Following the procedure described for Example 1, but substituting 7-hydroxycoumarin with the phenol from Step 3 and 3-[4-(4-methoxy)tetrahydropyranyl]-benzyl bromide with 3-[4-(4-hydroxy)tetrahydropyranyl]benzyl bromide as starting material, the title product was obtained as a solid, m.p. 183°-185° C.

Step 5: 3-(3-Thienyl)-3-{4-[3-(4-(4-hydroxy)tetrahydropyranyl)benzyloxy]-2-hydroxyphenyl}propenoic acid disodium salt Following the procedure described in Example 1, Step 2, but substituting the coumarin from Step 4 for 7-[3-(4-(4-methoxy)tetrahydropyranyl)benzyloxy]-coumarin as starting material, the title compound is obtained.

EXAMPLE 10

3-(3-Thienyl)-3-[4-[3-(4-(4-methoxy)tetrahydropyranyl)benzyloxy]-2-hydroxyphenyl}propenoic acid disodium salt Following the procedure described for Example 1, Steps 1 and 2, but substituting 7-hydroxycoumarin with 7-hydroxy-4-(3-thienyl)coumarin (from Example 9, Step 3) as starting material in Step 1, the title product was obtained as a solid.

$^1$H NMR (d$^6$ DMSO): δ 1.8-2.05 (m, 4H), 2.85 (s, 3H), 3.55-3.80 (m, 4H), 4.88 (s, 2H), 5.1 (d, 1H, J=7.5 Hz), 5.92 (s, 1H), 6.25 (s, 1H), 6.42 (d, 1H, J=7.5 Hz), 6.85 (d, 1H, J=3 Hz), 7.08 (d, 1H), J=3 Hz), 7.2-7.5 (m, 5H).

EXAMPLE 11

3-(3-Thienyl)-3-[4-[3-(4-(4-ethoxy)tetrahydropyranyl)benzyloxy]-2-hydroxyphenyl}propenoic acid disodium salt Following the procedure described for Example 1, Steps 1-2, but substituting 7-hydroxycoumarin with 7-hydroxy-4-(3-thienyl)coumarin (from Example 9, Step 3) and 3-[4-(4-methoxy)tetrahydropyranyl]benzyl bromide with 3-[4-(4-ethoxy)tetrahydropyranylbenzyl chloride as starting material in Step 1, the title compound is obtained.

EXAMPLE 12

3-(3-Thienyl)-3-{4-[3-(4-(4-cyclopropylmethoxy)tetrahydropyranyl)benzyloxy]-2-hydroxyphenyl} propenoic acid disodium salt Following the procedure for Example 1, Steps 1-2, but substituting 7-hydroxycoumarin with 7-hydroxy-4-(3-thienyl)coumarin (from Example 9, Step 3) and 3-[4-(4-methoxy)tetrahydropyranyl]benzyl bromide with 3-[4-(4-cyclopropylmethoxy)tetrahydropyranyl]benzyl chloride as starting material in Step 1, the title compound is obtained.

EXAMPLE 13

3-(3-Thienyl)-3-{4-[6-(4-(4-hydroxy)tetrahydropyranyl)pyridin-2-ylmethoxy]-2-hydroxyphenyl} propenoic acid disodium salt

Step 1: 7-[6-(4-(4-Hydroxy)tetrahydropyranyl)pyridin-2-yl methoxy]-4-(3-thienyl)coumarin To a solution of 7-hydroxy-4-(3-thienyl)coumarin from Example 9, Step 3 (180 mg), 6-[4-(4-hydroxy)tetrahydropyranyl)-pyridin-2-ylmethanol (155 mg) and triphenylphosphine (232 mg) in THF (5 mL) at r.t. was added azo-di-t-butyl dicarboxylate (202 mg). After 1 hr, further portions of triphenylphosphine (232 mg) and azo-di-t-butyl dicarboxylate (202 mg) were added and the reaction stirred for a further 1 hr. The mixture was concentrated and the residue chromatographed (50% EtOAc/hexane) to afford a solid. This solid was swished with ether and filtered to provide the title compound as a solid, m.p. 177°-180° C.

Step 2: 3-(3-Thienyl)-3-{4-[6-(4-(4-hydroxy)tetrahydropyranyl)pyridin-2-ylmethoxy]-2-hydroxyphenyl}propenoic acid disodium salt Following the procedure described in Example 1, Step 2, but substituting the coumarin from Step 1 for 7-[3-(4-(4-methoxy)tetrahydropyranyl)benzyloxy]-coumarin as starting material, the title compound is obtained.

EXAMPLE 14

3-(3-Thienyl)-3-{4-[6-(4-(4-methoxy)tetrahydropyranyl)pyridin-2-ylmethoxy]-2-hydroxyphenyl} propenoic acid disodium salt Step 1:

7-[6-(4-(4-Methoxy)tetrahydropyranyl)pyridin-2-ylmethoxy]-4-(3-thienyl)coumarin

To KH (293 mg; 30% in oil) in THF (3 mL) at r.t. was added 7-[6-(4-(4-hydroxy)tetrahydropyranyl)pyridin-2-ylmethoxy]-4(3-thienyl)coumarin (from Example 13, Step 1; 100 mg) in THF (3 mL). After 5 min, iodomethane (22 µL) was added and the reaction allowed to proceed over 5 hr with additional aliquots of iodomethane being added after each hour. When the reaction was completed, HOAc (250 µL) was added followed by sat.'d NH₄Cl solution and EtOAc. The organic phase was washed with brine, dried and evaporated. Chromatography (hexane/EtOAc 1:1) and subsequent crystallisation from Et₂O afforded the title compound as a solid, m.p. 105°–107° C.

Step 2:

3-(3-Thienyl)-3-{4-[6-(4-(4-methoxy)tetrahydropyranyl) pyridin-2-ylmethoxy]-2-hydroxyphenyl}propenoic acid disodium salt Following the procedure described in Example 1, Step 2, but substituting the coumarin from Step 1 for 7-[3-(4-(4-methoxy)tetrahydropyranyl)benzyloxy]-coumarin as starting material, the title compound is obtained.

EXAMPLE 15

[1S,5R]3-(3-Thienyl)-3-{4-[3-(3-(3α-hydroxy-6,8-dioxabicyclo[3.2.1]octanyl))benzyloxy]-2-hydroxyphenyl} propenoic acid disodium salt Step 1:

[1S,5R]7-{3-[3-(3α-Hydroxy-6,8-dioxabicyclo[3.2.1]octanyl)]-benzyloxy}-4-(3-thienyl)coumarin Following the procedure described for Example 13, Step 1, but substituting [1S,5R]3-[3-(3α-hydroxy-6,8-dioxabicyclo[3.2.1]octanyl)]benzyl alcohol with 6-[4-(4-hydroxy)tetrahydropyranyl]pyridin-2-ylmethanol as starting material, the title compound was obtained as a solid, m.p. 165°–167° C.

Step 2:

[1S,5R]3-(3-Thienyl)-3-{4-[3-(3-(3α-hydroxy-6,8-dioxabicyclo[3.2.1]octanyl))benzyloxy]-2-hydroxyphenyl} propenoic acid disodium salt Following the procedure described in Example 1, Step 2, but substituting the coumarin from Step 1 for 7-[3-(4-(4-methoxy)tetrahydropyranyl)benzyloxy]-coumarin as starting material, the title compound is obtained.

EXAMPLE 16

[1S,5R]3-(3-Thienyl)-3-{4-[3-(3-(3α-methoxy-6,8-dioxabicyclo[3.2.1]octanyl))benzyloxy]-2-hydroxyphenyl} propenoic acid disodium salt;

Step 1:

[1S,5R]7-{3-[3-(3α-Methoxy-6,8-dioxabicyclo[3.2.1]octanyl)]benzyloxy}-4-(3-thienyl)coumarin A solution of [1S,5R]7-{3-[3-(3α-Hydroxy-6,8-dioxabicyclo[3.2.1]octanyl)]benzyloxy}4-(3-thienyl)coumarin (from Example 15, Step 1; 250 mg) in THF (5 mL) was added to a suspension of KH (35% in oil, 325 mg) in THF (5 mL) and the mixture stirred under nitrogen for 10 min. Iodomethane (320 µL) was added followed by a further amount of iodomethane (200 µL) after 3 hr. After a total of 4 hr, the mixture was quenched with HOAc (600 µL), poured onto H₂O and extracted with EtOAc. The dried organic layer was concentrated and the residue chromatographed (hexane/EtOAc 1:1) to give (after a swish with Et₂O) the title compound was obtained as a solid, m.p. 133°–135° C.

Step 2:

[1S,5R]3-(3-Thienyl)-3-{4-[3-(3-(3α-methoxy-6,8-dioxabicyclo[3.2.1]octanyl))
benzyloxy]-2-hydroxyphenyl}propenoic acid disodium salt Following the procedure described in Example 1, Step 2, but substituting the coumarin from Step 1 for 7-[3-(4-(4-methoxy)tetrahydropyranyl)benzyloxy]-coumarin as starting material, the title compound was obtained as a solid.

$^1$H NMR (d$^6$ DMSO): δ 1.85–2.4 (m, 4H), 2.9 (s, 3H), 3.48–3.68 (m, 1H), 4.25 (d, 1H, J=7.5 Hz), 4.5–4.6 (m, 1H), 4.4 (s, 2H), 5.55 (s, 1H), 5.7 (s, 1H), 5.95 (s, 1H), 6.25 (s, 1H), 6.45 (d, 1H, J=7.5 Hz, 6.85 (d, 1H, J=3 Hz), 7.05 (d, 1H, J=3 Hz), 7.2–7.45 (m, 4H).

EXAMPLE 26

[1S,5R]3-(3-Thienyl)-3-{4-[6-(3-(3α-methoxy)-6,8-dioxabicyclo[3.2.1]octanyl)pyridin-2-ylmethoxy]-2-hydroxyphenyl}propenoic acid disodium salt Alcohol 10 was coupled with 7-hydroxy-4-(3-thienyl)coumarin (Example 9, Step 3) by the method of Example 13. The resulting alcohol was methylated by the procedure of Example 14, Step 1, and was hydrolysed as per Example 1, Step 2, to yield the title compound.

EXAMPLE 27

3-Phenyl-3-{4-[3-Fluoro-5-(4-(4-hydroxy)tetrahydropyranyl)phenoxymethyl]-2-hydroxyphenyl} propenoic acid disodium salt Step 1: 7-Hydroxy4-phenylcoumarin A mixture of resorcinol (20 g), ethyl benzoylacetate (23.8 mL) and O-phosphoric acid (130 mL) was heated at 85° C. with care for 1 hr. The solution was cooled, poured onto H₂O, extracted (3x EtOAc/THF), washed twice with H₂O, and then twice with brine. The organic phase was dried and evaporated. Trituration with Et₂O followed by filtration afforded the title compound as a solid.

Step 2: 4-Phenyl-7-trifluoromethanesulfonyloxycoumarin

To a solution of 7-hydroxy-4-phenylcoumarin from Step 1 (1.22 g) and Et$_3$N (1.05 mL) in CH$_2$Cl$_2$ (25 mL) at 0° C. was added trifluoro-methanesulfonic anhydride (1.6 g). After 30 min., the mixture was poured onto 1N HCl, extracted (3x EtOAc), washed with brine, dried, and evaporated. Purification on silica gel (hexane/EtOAc 2:1 ) gave the title compound.

Step 3: 7-Carbomethoxy-4-phenylcoumarin

A solution of 4-phenyl-7-trifluoromethanesulfonyloxycoumarin (1.75 g) and tetrakis (triphenylphosphine)palladium (0) (600 mg) in Et$_3$N (1.3 mL), MeOH (15 mL) and DMSO (25 mL) was stirred under an atmosphere of carbon monoxide for 1 hr at 70° C. The mixture was then poured onto sat'd. NH$_4$Cl solution, extracted with EtOAc, dried and evaporated. Chromatography on silica gel (30% EtOAc/hexane) yielded the title compound as a solid, m.p. 133°–135° C.

Step 4: 4-Phenyl-7-coumarincarboxylic acid

A mixture of 7-carbomethoxy-4-phenylcoumarin (510 mg), 1N LiOH (10 mL), THF (7 mL) and MeOH (10 mL) was heated at reflux for 1 hr. The solution was concentrated then H$_2$O (10 mL), 1N HCl (15 mL), THF (10 mL) and Et$_2$O (10 mL) were added and stirring continued for 1 hr. After this time, the organic layer was separated and concentrated to yield the title compound which was used as such in the next step.

Step 5: 7-Hydroxymethyl-4-phenylcoumarin

To a solution of 4-phenyl-7-coumarincarboxylic acid from Step 4 (550 mg) and Et$_3$N (560 μL) in THF (25 mL) at 0° C. was added isobutylchloroformate (560 μL) dropwise. After 45 min., NaBH$_4$ (185 mg) in H$_2$O was added and stirring continued for a further 20 min. The mixture was poured onto 1N HCl, extracted (3x Et$_2$O), dried, and evaporated. Chromatography on silica gel using hexane/EtOAc 1:1 afforded the title compound as a solid.

Step 6: 7-[3-Fluoro-5-(4-(4-hydroxy)tetrahydropyranyl)phenoxyrnethyl]4-phenylcoumarin Following the procedure described for Example 13 but substituting the alcohol from Step 5 for 7-hydroxy-4-(3-thienyl)coumarin and 3-fluoro-5-[4-(4-hydroxy)tetrahydropyranyl]phenol for 6-[4-(4-hydroxy)tetrahydropyranyl]pyridin-2-ylmethanol as starting material, the title compound was obtained as a solid, m.p. 134°–136° C.

Step 7: 3-Phenyl-3-{4-[3-Fluoro-5-(4-(4-hydroxy)tetrahydropyranyl)phenoxymethyl]-2-hydroxyphenyl} propenoic acid disodium salt Following the procedure described in Example 1, Step 2, but substituting the coumarin from Step 6 for 7-[3-(4-(4-methoxy)tetrahydropyranyl)benzyloxy]coumarin as starting material, the title compound is obtained.

EXAMPLE 29

3-(3-Thienyl)-3-{4-[3-fluoro-5-(4-(4-hydroxy)tetrahydropyranyl)phenoxymethyl]-2-hydroxyphenyl} propenoic acid disodium salt

Step 1: 7-Hydroxymethyl-4-(3-thienyl)coumarin

Following the procedure described in Example 27, Steps 2–5, but substituting 7-hydroxy-4-(3-thienyl)coumarin (from Example 9, Step 3) for 7-hydroxy-4-phenylcoumarin as starting material, the title product was obtained as a solid.

Step 2: 7-Chloromethyl-4-(3-thienyl)coumarin

To a solution of the alcohol from Step 1 (1.65 g) and hexamethylphosphorous triamide in 35 mL THF at 0° C. was added CCl$_4$ (1.3 mL) and the mixture stirred for 30 min. The mixture was diluted with Et$_2$O, filtered, concentrated and the residue chromatographed (30% EtOAc/hexane) to provide the title compound as a solid, m.p. 125°–127° C.

Step 3: 3-(3-Thienyl)-3-{4-[3-fluoro-5-(4-(4-hydroxy)tetrahydropyranyl) phenoxymethyl]-2-hydroxyphenyl} propenoic acid disodium salt Following the procedure described in Example 1, Steps 1–2, but substituting the chloride from Step 2 for 3-[4-(4-methoxy)tetrahydropyranyl]benzyl bromide and 3-fluoro-5-[4-(4-hydroxy)tetrahydropyranyl]phenol (alcohol 11 ) for 7-hydroxycoumarin in Step 1, the title product was obtained as a solid.

$^1$H NMR (d$^6$ DMSO): δ 1.48 (d, 2H, J=13.5 Hz), 1.85–2.0 (m, 2H), 3.6–3.8 (m, 4H), 4.8 (s, 2H), 5.3 (s, 1H), 6.1 (d, 1H, J=3 Hz), 6.25–6.40 (m, 2H), 6.6 (d, 1H, J=7.5 Hz), 6.7 (d, 1H, J=11.2 Hz), 6.75–6.85 (m, 2H), 6.95 (s, 1H), 7.1 (d, 1H, J=7.5 Hz), 7.25–7.35 (m, 1H).

EXAMPLE 30

3-(3-Thienyl)-3-{4-[3-fluoro-5-(4-(4-methoxy)tetrahydropyranyl)phenoxymethyl]-2-hydroxyphenyl} propenoic acid disodium salt

Step 1: 7-[3-Fluoro-5-(4-(4-methoxy)tetrahydropyranyl) phenoxymethyl]-4-(3-thienyl)coumarin Following the procedure described for Example 14, Step 1, but substituting 7-[3-fluoro-5-(4-(4-hydroxy)tetrahydropyranyl)phenoxymethyl]-4-(3-thienyl)coumarin from Example 29, Step 3, for 7-[6-(4-(4-hydroxy)tetrahydropyranyl)pyridin-2-ylmethoxy]-4-(3-thienyl)coumarin as starting material, the title compound was obtained as a solid, m.p. 153°–155° C.

Step 2: 3-(3-Thienyl)-3-{4-[3-fluoro-5-(4-(4-methoxy)tetrahydropyranyl)phenoxymethyl]-2-hydroxyphenyl} propenoic acid disodium salt Following the procedure described in Example 1, Stop 2, but substituting the coumarin from Step 1 for 7-[3-(4-(4-methoxy)tetrahydropyranyl)benzyloxy]coumarin as starting material, the title compound is obtained.

EXAMPLE 35

[1S,5R]3-(3-Thienyl)-3-{4-[3-fluoro-5-(3-(3α-hydroxy-6,8-dioxabicyclo[3.2.1]octanyl))phenoxymethyl]-2-hydroxyphenyl}propenoic acid disodium salt Following the procedure described for Example 1, Steps 1–2, but substituting [1S,5R]3-fluoro-5-[3-(3α-hydroxy-6,8-dioxabicyclo[3.2.1]octanyl)]phenol for 7- hydroxycoumarin and 7-chloromethyl-4-(3-thienyl)-coumarin (from Example 29, Step 2) for 3-[4-(4-methoxy)tetrahydropyrano]benzyl bromide as starting material in Step 1, the title compound was obtained.

$^1$H NMR (d$^6$ DMSO, d$^6$ acetone): δ 1.75–2.25 (m, 4H), 3.5–3.6 (m, 1H), 4.40 (d, 1H), 4.55–4.65 (m, 1H) 4.85 (brs, 2H), 5.2 (s, 1H), 5.58 (s, 1H), 6.0–6.95 (m, 7H), 6.35 (s, 1H), 7.05–7.15 (m, 1H) 7.3–7.4 (m, 1H).

EXAMPLE 36

[1S,5R]3-(3-Thienyl)-3-{4-[3-fluoro-5-(3-(3α-methoxy-6,8-dioxabicyclo[3.2.1]octanyl))phenoxymethyl]-2-hydroxyphenyl}propenoic acid disodium salt.

Following the procedure described for Example 1, Steps 1–2, but substituting [1S,5R]3-fluoro-5-[3-(3α-methoxy-6,8-dioxabicyclo[3.2.1]octanyl)]phenol for 7-hydroxycoumarin and 7-chloromethyl-4-(3-thienyl)coumarin (from Example 29, Step 2) for 3-[4-(4-methoxy)tetrahydropyranyl]benzyl bromide as starting material in Step 1, the title compound was obtained.

$^1$H NMR (d$^6$ DMSO): δ 1.85–2.35 (m, 4H), 2.9 (s, 3H), 3.48–3.6 (m, 1H), 4.21 (d, 1H, J=7.5 Hz), 4.5–4.6 (m, 1H), 4.9 (s, 2H), 5.55 (s, 1H), 6.35 (s, 1H), 6.6–6.9 (m, 7H), 7.0–7.1 (m, 1H), 7.3–7.4 (m, 1H).

EXAMPLE 37

3-(3-Furyl)-3-{4-[3-fluoro-5-(3-(3α-hydroxy-6,8-dioxabicyclo[3.2.1]octanyl))phenoxymethyl]-2-hydroxyphenyl}propenoic acid disodium salt Step 1:

[1S,5R]7-{3-Fluoro-5-[3-(3α-hydroxy-6,8-dioxabicyclo[3.2.1]octanyl)]phenoxymethyl}-4-(3-furyl)coumarin Following procedures described in Example 1, Alcohol 12 was coupled with halide 9 to yield the title compound, m.p. 123°–124° C.

Analysis calculated for C$_{26}$H$_{21}$FO$_7$: C, 67.24; H, 4.56. Found: C, 67.39; H, 4.53.

Step 2:

3-(3-Furyl)-3-{4-[3-fluoro-5-(3-(3α-hydroxy-6,8-dioxabicyclo[3.2.1]octanyl))phenoxymethyl]-2-hydroxyphenyl}propenoic acid disodium salt Following the procedure of Example 1, Step 2, the compound of Step 1 was converted to the title compound.

EXAMPLE 49

[1S,5R]3-(3-Thienyl)-3-{4-[5-(3-(3α-hydroxy-6,8-dioxabicyclo[3.2.1]octanyl))phenoxymethyl]-2-hydroxyphenyl]propenoic acid disodium salt Following the procedure described for Example 1, but substituting [1S,5R]3-[3-(3α-hydroxy-6,8-dioxabicyclo[3.2.1]octanyl)]phenol for 7-hydroxycoumarin and 7-chloromethyl-4-(3-thienyl)coumarin (from Example 29, Step 2) for 3-[4-(4-methoxy)tetrahydropyranyl]benzyl bromide as starting material, the title compound was obtained as a glass.

$^1$H NMR (d$^6$ DMSO, d$^6$ acetone): δ 1.8–2.4 (m, 4H), 3.55–3.65 (m, 1H), 4.52 (d, 1H, J=7.5 Hz) 4.55–4.62 (m, 1H), 5.05 (s, 2H) 5.55 (s, 1H), 6.55 (s, 1H), 6.78–7.1 (m, 7H), 7.15–7.28 (m, 2H), 7.3–7.4 (m, 1H).

EXAMPLE 50

(1S,5R]3-(3-Thienyl)-3-{4-[5-(3-(3α-methoxy-6,8-dioxabicyclo[3.2.1]octanyl))phenoxymethyl]-2-hydroxyphenyl]propenoic acid disodium salt Following the procedure described for Example 1, but substituting [1S,5R]3-[3-(3α-methoxy-6,8-dioxabicyclo[3.2.1]octanyl)]phenol for 7-hydroxycoumarin and 7-chloromethyl-4-(3-thienyl)coumarin (from Example 29, Step 2) for 3-[4-(4-methoxy)tetrahydropyranyl]benzyl bromide as starting material, the title compound was obtained as a glass.

$^1$H NMR (d$^6$ DMSO, d$^6$ acetone): δ 1.95–2.38 (m, 4H), 2.95 (s, 3H), 3.52–3.60 (m, 1H), 4.32 (d, 1H, J=7.5 Hz), 4.5–4.6 (m, 1H), 5.05 (s, 2H), 5.55 (s, 1H), 6.48 (s, 1H), 6.75–7.05 (m, 8H), 7.2–7.4 (m, 2H).

EXAMPLE 51

3-Phenyl-3-{4-[3-(4-(4-methoxy)tetrahydropyranyl)-benzyloxy]-2-hydroxyphenyl}propanoic acid disodium salt Step 1:

7-[3-(4-(4-Methoxy)tetrahydropyranyl)benzyloxy]-4-phenyl-3,4-dihydrocoumarin

To a solution of 7-[3-(4-(4-methoxy)tetrahydropyranyl)benzyloxy]-4-phenylcoumarin (from Example 6; 142 mg) in THF (2.5 mL) and MeOH (2.5 mL) was added 10% Pd-C and the mixture placed under an atmosphere of H$_2$. After 3 hr, the mixture was filtered through celite and the solvent removed. Chromatography of the residue (silica gel; hexane/EtOAc 2:1) afforded the title compound as a foam; m/e required for C$_{28}$H$_{28}$O$_5$: 444; found: 444.

Step 2:

3-Phenyl-3-{4-[3-(4-(4-methoxy)tetrahydropyranyl)-benzyloxy]-2-hydroxyphenyl}propanoic acid disodium salt Following the procedure described in Example 1, Step 2, but substituting the coumarin from Step 1 for 7-[3-(4-(4-methoxy)tetrahydropyranyl)benzyloxy] coumarin as starting material, the title compound was obtained.

Analysis: Calc'd for C$_{28}$H$_{28}$O$_6$Na$_2$.1H$_2$O: C, 64.12; H, 5.77. Found: C, 64.10; H, 5.71.

EXAMPLE 52

(+)3-(3-Thienyl)-3-{4-[3-fluoro-5-(3-(3α-hydroxy-5-methyl-6,8-dioxabicyclo[3.2.1]octanyl))phenoxymethyl]-2-hydroxyphenyl}propenoic acid disodium salt Step 1:

(+)7-{3-Fluoro-5-[3-(3α-hydroxy-5-methyl-6,8-dioxabicyclo[3.2.1]octanyl)]phenoxymethyl}-4-(3-thienyl)-coumarin Reacting Alcohol 16 with 7-chloromethyl-4-(3-thienyl) coumarin (Example 29, Step 2), according to the procedure of Example 1, yielded the title compound.

Mass spectrum=M+ =495

Step 2:

(+)3-(3-Thienyl)-3-{4-[3-fluoro-5-(3-(3α-hydroxy-5-methyl-6,8-dioxabicyclo[3.2.1]octanyl))phenoxymethyl]-2-hydroxyphenyl}propenoic acid disodium salt Treatment of the compound of Step 1 according to the procedure of Example 1, Step 2, yields the title compound.

EXAMPLE 53

3-(3-Thienyl)-3-{4-[3-bromo-5-(4-(4-methoxy)tetrahydropyranyl)phenoxymethyl]-2,hydroxyphenyl} propenoic acid disodium salt

Step 1:
7-[3-Bromo-5-(4-(4-methoxy)tetrahydropyranyl)-phenoxymethyl]-4-(3-thienyl)coumarin.

Using the above procedures, the title compound was prepared, m.p. 201°–202° C.

Step 2:
3-(3-Thienyl)-3-{4-[3-bromo-5-(4-(4-methoxy)tetrahydropyranyl)-phenoxymethyl]-2-hydroxyphenyl} propenoic acid disodium salt Using the compound from Step 1, the procedure of Example 1, Step 2, yields the title compound.

EXAMPLES 17–26, 28, 31–34, AND 38–48

Examples 17–26, 28, 31–34 and 38–48 may be prepared by coupling the appropriate coumarin derivative with a substituted benzylic halide, benzylic alcohol or phenol using the procedures described in the preceding examples. The coumarins may then be converted to the corresponding disodium salt by following the procedure given in Example 1, Step 2.

What is claimed is:

1. A compound of the Formula I:

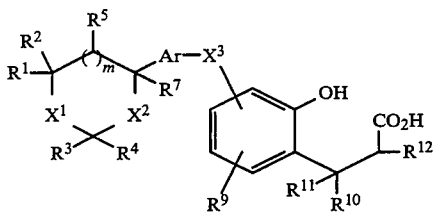

wherein:

$R^1$ is H, OH, lower alkyl, or lower alkoxy;
$R^2$ is H, lower alkyl or together with $R^1$ forms a double bonded oxygen (=O);
$R^3$ is H, lower alkyl, hydroxy lower alkyl, or lower alkoxy lower alkyl; or $R^1$ is joined to $R^3$ to form a carbon bridge of 2 or 3 carbon atoms, or a mono-oxa carbon bridge of 1 or 2 carbon atoms, said bridge optionally containing a double bond;
$R^4$ is H or lower alkyl;
$R^5$ is H, OH, lower alkyl, or lower alkoxy;
$R^6$ is H or lower alkyl, or two $R^6$ groups attached to the same carbon may form a saturated ring of 3 to 8 members;
$R^7$ is H, OH, lower alkyl, lower alkoxy, cycloalkyl lower alkoxy, lower alkylthio, or lower alkylcarbonyloxy;
$R^8$, $R^9$, and $R^{13}$ is each independently H, halogen, lower alkyl, hydroxy, lower alkoxy, lower alkylthio, $CF_3$, CN, or $COR^{14}$;
$R^{10}$ is H, lower alkyl, or aryl-$(R^{13})_2$, wherein aryl is a 5-membered aromatic ring wherein one carbon atom is replaced by O or S and 0–3 carbon atoms are replaced by N; a 5-membered aromatic ring wherein 1–4 carbon atoms are replaced by N; a 6-membered aromatic ring wherein 0–3 carbon atoms are replaced by N; 2- or 4-pyranone; 2- or 4-pyridinone; or a bicyclic 8-, 9-, or 10-membered aromatic ring wherein 0–2 carbon atoms are replaced by either O or S or a combination thereof and 0–3 carbon atoms are replaced by N;
$R^{11}$ and $R^{12}$ is each independently H or lower alkyl, or $R^{11}$ and $R^{12}$ together form a bond;
$R^{14}$ is H or lower alkyl;
$X^1$ is O, S, S(O), S(O)2, or CH2;
$X^2$ is O, S, or CHR6;
$X^3$ is $OC(R^6)_2$ or $C(R^6)_2O$;
Ar is arylene-$(R^8)_2$, wherein arylene is phenyl;
m is 1;
n is 1 or 2;
or a pharmaceutically acceptable salt thereof.

2. A compound of claim 1 of the Formula Ia:

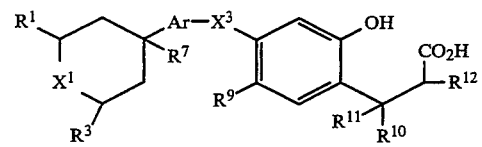

wherein:

$R^1$ and $R^3$ is each independently H or $CH_3$, or together are $-CH_2CH_2-$, $-CH_2O-$, or $-OCH_2-$;
$R^7$ is OH, OMe, OEt, or OCH2c-Pr;
$R^9$ is H or Cl;
$R^{10}$ is H, Me, Pr, Ph, 3-Fu, or 3-Th;
$R^{11}$ and $R^{12}$ is each H, or $R^{11}$ and $R^{12}$ together are a bond;
$X^3$ is $-CH_2O-$ or $-OCH_2-$; and
Ar is 3-Phe.

3. A compound of claim 1 of the Formula Ib:

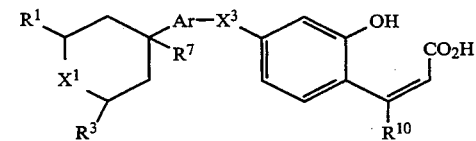

wherein:

$R^1$ and $R^3$ is each H or together are $-CH_2O$ or $-OCH_2-$;
$R^7$ is OH or OMe;
$R^{10}$ is Ph, 3-Fu, or 3-Th;
$X^3$ is $-CH_2O-$ or $-OCH_2-$;
Ar is 3-Phe.

4. A compound of claim 1 of the Formula Ic:

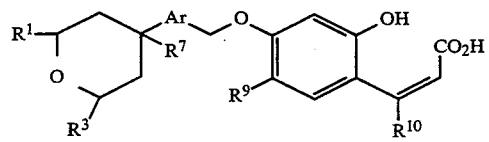

wherein the substituents are as follows:

| EX. | $R^1$ | $R^3$ | $R^7$ | $R^9$ | $R^{10}$ | Ar |
|---|---|---|---|---|---|---|
| 1 | H | H | OMe | H | H | 3-Phe |
| 2 | H | H | OMe | H | Me | 3-Phe |
| 3 | H | H | OMe | Cl | Me | 3-Phe |
| 4 | H | H | OMe | H | n-Pr | 3-Phe |
| 5 | H | H | OH | H | Ph | 3-Phe |
| 6 | H | H | OMe | H | Ph | 3-Phe |
| 7 | H | H | OH | H | 3-Fu | 3-Phe |
| 8 | H | H | OMe | H | 3-Fu | 3-Phe |
| 9 | H | H | OH | H | 3-Th | 3-Phe |
| 10 | H | H | OMe | H | 3-Th | 3-Phe |

-continued

| EX. | R¹ | R³ | R⁷ | R⁹ | R¹⁰ | Ar |
|---|---|---|---|---|---|---|
| 11 | H | H | OEt | H | 3-Th | 3-Phe |
| 12 | H | H | OCH₂c-Pr | H | 3-Th | 3-Phe |
| 15 | —CH₂O— | | OH | H | 3-Th | 3-Phe |
| 16 | —CH₂O— | | OMe | H | 3-Th | 3-Phe |
| 17 | —CH₂O— | | OH | H | 3-Fu | 3-Phe |
| 18 | —CH₂O— | | OMe | H | 3-Fu | 3-Phe |
| 19 | —CH₂O— | | OH | H | Ph | 3-Phe |
| 20 | —CH₂O— | | OMe | H | Ph | 3-Phe |
| 21 | —CH₂CH₂— | | OH | H | 3-Th | 3-Phe |
| 22 | —CH₂CH₂— | | OME | H | 3-Th | 3-Phe. |

5. A compound of claim 1 of the Formula Id:

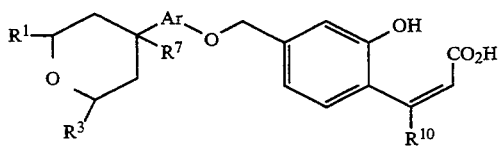

wherein the substituents are as follows:

| EX. | R¹ | R³ | R⁷ | R¹⁰ | Ar |
|---|---|---|---|---|---|
| 27 | H | H | OH | Ph | 5-(3-FPhe) |
| 28 | H | H | OMe | Ph | 5-(3-FPhe) |
| 29 | H | H | OH | 3-Th | 5-(3-FPhe) |

-continued

| EX. | R¹ | R³ | R⁷ | R¹⁰ | Ar |
|---|---|---|---|---|---|
| 30 | H | H | OMe | 3-Th | 5-(3-FPhe) |
| 31 | H | H | OH | 3-Fu | 5-(3-FPhe) |
| 32 | H | H | OMe | 3-Fu | 5-(3-FPhe) |
| 33 | —CH₂O— | | OH | Ph | 5-(3-FPhe) |
| 34 | —CH₂O— | | OMe | Ph | 5-(3-FPhe) |
| 35 | —CH₂O— | | OH | 3-Th | 5-(3-FPhe) |
| 36 | —CH₂O— | | OMe | 3-Th | 5-(3-FPhe) |
| 37 | —CH₂O— | | OH | 3-Fu | 5-(3-FPhe) |
| 38 | —CH₂O— | | OMe | 3-Fu | 5-(3-FPhe) |
| 39 | —CH₂CH₂— | | OH | 3-Th | 5-(3-FPhe) |
| 40 | —CH₂CH₂— | | OMe | 3-Th | 5-(3-FPhe) |
| 49 | —CH₂O— | | OH | 3-Th | 3-Phe |
| 50 | —CH₂O— | | OMe | 3-Th | 3-Phe |
| 53 | H | H | OMe | 3-Th | 5-(3-BrPhe). |

6. A compound of claim 1 which is 3-phenyl-3-{4-[3(4-(4-methoxy)tetrahydropyranyl)benzyloxy]-2-hydroxyphenyl}propanoic acid disodium salt.

7. A compound of claim 1 which is (+) 3-(3-thienyl)-3{4-[3-fluoro-5-(3-(3α-hydroxy-5-methyl-6,8-dioxabicyclo[3.2.1]octanyl))phenoxymethyl]-2-hydroxyphenyl} propenoic acid disodium salt.

8. A pharmaceutical composition comprising a therapeutically effective amount of a compound of claim 1 and a pharmaceuitcally acceptable carrier.

9. A method of preventing the synthesis of leukotrienes in a mammal which comprises administering to said mammal an effective amount of a compound of claim 1.

10. A method of claim 9 wherein the mammal is man.

* * * * *